(12) United States Patent
Schnute

(10) Patent No.: US 6,653,307 B2
(45) Date of Patent: Nov. 25, 2003

(54) 1-ARYL-4-OXO-1,4-DIHYDRO-3-QUINOLINECARBOXAMIDES AS ANTIVIRAL AGENTS

(75) Inventor: Mark E. Schnute, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 331 days.

(21) Appl. No.: 09/875,432

(22) Filed: Jun. 5, 2001

(65) Prior Publication Data

US 2002/0103220 A1 Aug. 1, 2002

Related U.S. Application Data

(60) Provisional application No. 60/212,202, filed on Jun. 16, 2000, and provisional application No. 60/272,136, filed on Feb. 28, 2001.

(51) Int. Cl.⁷ ..................... A61K 31/5377; A61P 31/22; C07D 413/14
(52) U.S. Cl. ..................... 514/235.2; 544/80; 544/128; 544/546; 544/156
(58) Field of Search ................... 544/80, 128; 546/156; 514/235.2

(56) References Cited

U.S. PATENT DOCUMENTS

| | | |
|---|---|---|
| 4,786,664 A | 11/1988 | Glamkowski et al. |
| 4,956,465 A | 9/1990 | Schriewer et al. |
| 4,959,363 A | 9/1990 | Wentland |
| 5,175,151 A | 12/1992 | Afonso et al. |
| 5,328,887 A | 7/1994 | Janssens |
| 5,622,967 A | 4/1997 | Dolle et al. |
| 5,753,666 A | 5/1998 | Beasley et al. |
| 5,891,878 A | 4/1999 | Beasley et al. |
| 6,015,789 A | 1/2000 | Suzuki et al. |

FOREIGN PATENT DOCUMENTS

| | | |
|---|---|---|
| EP | 370686 B1 | 11/1989 |
| EP | 612731 A1 | 1/1994 |
| EP | 945435 A1 | 8/1999 |
| GB | 1191443 | 5/1970 |
| GB | 2236751 A | 4/1991 |
| JP | 44012143 | 9/1966 |
| JP | 02124871 | 5/1990 |
| WO | WO96/16046 | 5/1996 |
| WO | WO97/04775 | 2/1997 |
| WO | WO98/23608 | 6/1998 |
| WO | WO99/32450 | 7/1999 |

OTHER PUBLICATIONS

Wentland, Mark P. et al., *Drug Design and Discovery.* "Antiviral Properties of 3–Quinolinecarboxamides" A Series of Novel Non–Nucleoside Antiherpetic Agents. 1997, vol. 15, pp 25–38.

Wentland, Mark P. Et. Al., *Journal of Medicinal Chemistry.* Cyclic Variations of 3–Quinolinecarboxamides and Effects on Antiherpetic Activity. 2541–2545, 38, 1995.

Wentland, Mark P. Et. Al., *Journal of Medicinal Chemistry.* 3–Quinolinecarboxamides A Series of Novel Orally–Active Antiherpetic Agents. 1580–1596, 36, 1993.

*Primary Examiner*—Robert W. Ramsuer
(74) *Attorney, Agent, or Firm*—Lucy X. Yang

(57) ABSTRACT

The present invention provides compounds of formula I

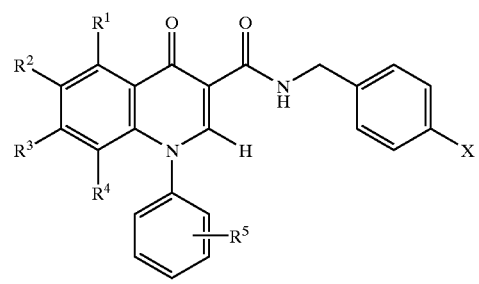

which are useful as antiviral agents, in particular, as agents against viruses of the herpes family.

32 Claims, No Drawings

1-ARYL-4-OXO-1,4-DIHYDRO-3-QUINOLINECARBOXAMIDES AS ANTIVIRAL AGENTS

CROSS REFERENCE TO RELATED APPLICATIONS

This application claims the benefit of the following provisional applications: U.S. Serial No. 60/212,202, filed Jun. 16, 2000, and No. 60/272,136, filed Feb. 28, 2001, under 35 USC 119(e)(i).

BACKGROUND OF THE INVENTION

1. Field of the Invention

The present invention provides 1-aryl-4-oxo-1,4-dihydro-3-quinolinecarboxamide derivatives. These compounds are useful as antiviral agents, in particular, as agents against viruses of the herpes family.

2. Technology Description

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6,7, and 8 (HHV-6, HHV-7, and HHV-8), have been shown to infect humans. HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Commonly assigned PCT/US99/27959 discloses specific 4-oxo-1,4-dihydro-3-quinolinecarboxamide as antiviral agents.

Commonly assigned PCT/US99/27960 discloses specific quinolinecarboxamide as antiviral agents.

Commonly assigned WO99/32450 discloses specific 4-hydroxyquinoline-3-carboxamides and hydrazides as antiviral agents.

U.S. Pat. No. 4,959,363 discloses specific quinolonecarboxamide compounds, their preparation and use as antivirals.

U.S. Pat. No 5,622,967 discloses specific quinolonecarboxamide calpain inhibitors useful in the treatment of neurodegenerative diseases.

MPWentland et. al. has disclosed on a number of occasions specific 3-quinolinecarboxamides and their effect on antiherpetic activity. Relevant references include Des. Discovery 1997, 15, 25–38 (Antiviral properties of 3-quinolinecarboxamides: a series of novel non-nucleoside antiherpetic agents); J. Med. Chem. 1993, 36, 1580–1596 (3-Quinolinecarboxamides. A series of novel orally-active antiherpetic agents); and J. Med. Chem. 1995, 38, 2541–2545 (Cyclic variations of 3-quinolinecarboxamides and effects on antiherpetic activity).

GB 1,191,433 discloses specific quinolone derivatives as antiviral agents.

EP 612731 discloses specific quinolone and naphthyridinonecarboxylic acids compounds as antiviral agents.

U.S. Pat. No. 5,328,887 discloses specific quinolin-2-one and quinolin-4-one compounds and derivatives thereof for use as fluorescent donor elements in thermal transfer processes.

U.S. Pat. No. 5,175,151 discloses specific quinolone derivatives as antiviral and antihypertensive agents.

U.S. Pat. No. 5,753,666 and 5,891,878 and WO 97/04775 disclose specific I-alkyl-substituted-quinolone-3-carboxamides that are alleged to have therapeutic utility via inhibition of Phosphodiesterase IV esterase and/or Tumor Necrosis factor activity.

U.S. Pat No. 6,015,789 discloses specific thienopyridinones as GnRH agonists and antagonists for use in treating sex-hormone dependent diseases.

EP 945435 discloses specific novel pyridonecarboxylic acid derivatives as bactericides.

GB 2236751 discloses specific 4-oxoquinolines and analogs as 5-HT3 antagonists for use in the treatment of neuro-psychiatric disorders.

U.S. Pat. No. 4,876,644 discloses specific 1-aryl-3-quinolinecarboxarnides useful for the treatment of pain.

JP 02124871 discloses specific quinolonecarboxamides and analogs as 5-lipoxygenase inhibitors.

WO96/16046 discloses specific benzyl pyrimidines useful as antibiotics.

JP 44012143 discloses specific 3-quinolinecarboxylic acid compounds with anti-inflammatory properties.

WO98/23608 discloses specific compounds which are fused heterocycles useful as antagonists for the $\alpha_v\beta_3$ and related integrin receptors.

U.S. Pat. No. 4,956,465 discloses specific quinoline and 1,8-naphthyridin-4-onecarboxylic acid which are C-bonded in the 7-position useful as antibacterials.

EP 370686 discloses a process for preparing specific quinoline carboxylic acid derivatives.

Despite the above teachings, there still exists a need in the art for novel compounds that demonstrate desirable antiviral activity.

BRIEF SUMMARY OF THE INVENTION

In accordance with the present invention, novel compounds which demonstrate antiviral activity are provided. More specifically, the compounds are specific 1-aryl-4-oxo-1,4-dihydro-3-quinolinecarboxamide derivatives which are useful as antiviral agents, particularly against herpes viruses.

Even more specifically, the present invention provides a compound of formula I,

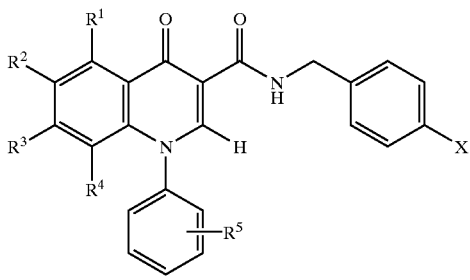

wherein,

X is Cl, F, Br, CN, or NO$_2$;

R$^1$ is H, halo, or Cl$_4$alkyl optionally substituted by one to three halo;

R$^2$ is
(a) H,
(b) halo,
(c) aryl,
(d) het, wherein said het is bound via a carbon atom,
(e) C$_{1-7}$alkyl which may be partially unsaturated and optionally substituted by one or more substituents of the group R$^{10}$, NR$^7$R$^1$, halo, (C=O)R, or S(O)$_m$R$^6$,
(f) NR$^7$R$^8$,
(g) OR$^{11}$,
(h) SR$^{11}$,
(i) NHSO$_2$R$^6$,
(j) S(O)$_m$R$^6$,
(k) (C=O)R$^1$,
(l) (C=O)OR$^1$,
(m) CHO,
(n) cyano, or
(o) C$_{3-8}$cycloalkyl which may be partially unsaturated and optionally substituted by one or more substituents selected from halo, oxo, R$^{10}$, C$_{1-7}$alkyl, or NR$^7$R$^8$;

R$^3$ is
(a) H,
(b) halo,
(c) OR$^{11}$, or
(d) C$_{1-7}$ alkyl which may be partially unsaturated and optionally substituted by one or more substituents of the group OR$^{11}$, SR$^{11}$, NR$^7$R$^8$, or halo, or R$^2$ together with R$^3$ form a carbocyclic or saturated 5 or 6 membered het which may be optionally substituted by NR$^7$R$^8$, het attached through a carbon atom, or C$_{1-7}$alkyl which may be optionally substituted by OR$^{12}$;

R$^4$ is
(a) H,
(b) halo,
(c) OR$^{11}$,
(d) C$_{1-7}$ alkyl which may be partially unsaturated and optionally substituted by one or more substituents of the group OR$^{11}$, SR$^{11}$, NR$^7$R$^8$, aryl, halo, C$_{3-8}$cycloalkyl optionally substituted by OR$^{12}$, or het attached through a carbon atom, or
(e) NR$^7$R$^8$;

R$^5$ is
(a) H,
(b) halo,
(c) OR$^{11}$,
(d) O(CH$_2$CH$_2$O)$_n$R$^{12}$,
(e) C$_{3-8}$cycloalkyl which may be partially unsaturated and is optionally substituted by one or more substituents selected from halo, OR$^{12}$, SR$^{12}$ oxo, C$_{1-7}$alkyl, or NR$^{12}$R$^{12}$,
(f) het,
(g) aryl,
(h) NHSO$_2$R$^6$,
(i) S(O)$_m$R,
(j) (C=O)R$^6$,
(k) (C=O)OR$^{11}$,
(l) nitro,
(m) cyano,
(n) SR$^{11}$,
(o) NR$^7$R$^8$,
(p) C$_{1-7}$alkyl which may be partially unsaturated and is optionally substituted by one or more substituents selected from NR$^7$R$^8$, R$^{10}$, S(O)$_m$R$^6$, (P=O)(OR$^{12}$)$_2$, (C=O)R$^6$, or halo,
(q) CHO,
(r) SCN,
(s) any two adjacent R$^5$ substituents taken with the bond connecting them to form an aryl, or het, or
(t) any two adjacent R$^5$ substituents taken together constitute a C$_{3-6}$alkyl chain which may be optionally substituted by R$^9$, NR$^7$R$^8$, cyano, CO$_2$R$^{12}$, OR$^{11}$, SR$^{11}$, or (=O);

R$^6$ is
(a) C$_{1-7}$alkyl,
(b) NR$^{11}$R$^{11}$,
(c) aryl, or
(d) het;

R$^7$ and R$^8$ are independently
(a) H,
(b) aryl,
(c) C$_{1-7}$ alkyl which may be partially unsaturated and is optionally substituted by one or more substituents selected from S(O)$_m$R$^6$, CONR$^{12}$R$^{12}$, CO$_2$R$^{12}$, (C=O)R$^9$, het, aryl, cyano, or halo,
(d) C$_{2-7}$alkyl which may be partially unsaturated and is substituted by one or more substituents selected from NR$^{12}$R$^{12}$, OR$^{11}$, or SR$^{11}$,
(e) C$_{3-8}$cycloalkyl which may be partially unsaturated and is optionally substituted by one or more substituents selected from halo, OR$^{12}$, SR$^{12}$, oxo, or NR$^{12}$R$^{12}$,
(f) (C=O)R$^9$, or
(g) R$^7$ and R$^8$ together with the nitrogen to which they are attached for a het;

R$^9$ is
(a) aryl,
(b) het, wherein said het is bound through a carbon atom,
(c) C$_{1-7}$alkyl optionally substituted by aryl, het, cyano, OR$^{12}$, SR$^{12}$, NR$^{12}$R$^{12}$, or halo, or
(d) C$_{3-8}$cycloalkyl which may be partially unsaturated and is optionally substituted by one or more substituents selected from halo, OR$^{12}$, SR$^{12}$, or NR$^{12}$R$^{12}$;

R$^{10}$ is
(a) OR$^{11}$,
(b) SR$^{11}$,
(c) CO$_2$R$^{12}$,
(d) het,
(e) aryl, or
(f) cyano;

$R^{11}$ is
- (a) H,
- (b) aryl,
- (c) het, wherein said het is bound through a carbon atom,
- (d) $C_{1-7}$alkyl optionally substituted by aryl, het wherein said het is bound through a carbon atom, $C_{3-8}$cycloalkyl optionally substituted by $OR^{12}$, or halo,
- (e) $C_{2-7}$alkyl substituted by $OR^{12}$, $SR^{12}$, or $NR^{12}R^{12}$, or
- (f) $C_{3-8}$cycloalkyl which may be partially unsaturated- and is optionally substituted by one or more substituents selected from halo, $OR^{12}$, $SR^{12}$, or $NR^{12}R^{12}$;

$R^{12}$ is H, or $C_{1-7}$alkyl;

each m is independently 1 or 2;

each n is independently 1, 2, or 3;

wherein aryl is a phenyl radical or an ortho-fused bicyclic carbocyclic radical wherein at least one ring is aromatic and is optionally substituted with one or more substituents selected from halo, OH, cyano, $CO_2R^{12}$, $CF_3$, $C_{1-6}$alkoxy, or $C_{1-6}$alkyl which may be further substituted by one to three $SR^{12}$, $NR^{12}R^{12}$, $OR^{12}$, or $CO_2R^{12}$ groups;

wherein het is a four-(4), five-(5), six-(6), or seven-(7) membered saturated or unsaturated heterocyclic ring having 1, 2, or 3 heteroatoms selected from oxygen, sulfur, or nitrogen, which is optionally fused to a benzene ring, or any bicyclic heterocyclic group and wherein any het is optionally substituted with one or more substituents selected from halo, OH, cyano, phenyl, $CO_2R$ 2, $CF_3$, $C_{1-6}$alkoxy, oxo, oxime, or $C_{1-6}$ alkyl which may be further substituted by one to three SR -, NR R $OR^1$, or $CO_2R$ groups; and wherein halo is F, Cl, Br or I;

and pharmaceutically acceptable salts thereof.

In particularly preferred embodiments, X is Cl and $R^2$ is 4-morpholinylmethyl. In still other preferred embodiments, either $R^2$ or $R^4$ or both $R^2$ and $R^4$ do not represent H. Another embodiment of the present invention provides a pharmaceutical composition comprising a compound of formula (I) as defined above, or a pharmaceutically acceptable salt thereof, and a pharmaceutically acceptable carrier. In preferred embodiments, the composition preferably comprises a therapeutically effective amount of the compound or salt.

Still another embodiment of the present invention provides a method for treating a disease or condition in a mammal caused by a viral infection, particularly a herpes viral infection, comprising administering to the mammal a therapeutically effective amount of a compound of formula (I) or a pharmaceutically acceptable salt thereof.

A further embodiment of the present invention comprises the use of a compound of formula (I) or a pharmaceutically acceptable salt thereof to prepare a medicament for treating or preventing diseases or disorders caused by a viral infection, and particularly a herpes viral infection.

A final embodiment of the present invention comprises a method for inhibiting a viral DNA polymerase, comprising contacting (in vitro or in vivo) the polymerase with an effective inhibitory amount of a compound of formula (I) or a pharmaceutically acceptable salt thereof.

An object of the present invention is to provide novel compounds having biological activity.

A further object of the present invention is to provide novel pharmaceutical compositions.

Still another object of the present invention is to provide a method for treating a disease or condition in a mammal caused by a viral infection, particularly a herpes virus infection.

Another object of the present invention is to provide a method for inhibiting a viral DNA polymerase.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g., 1, 2, 3, or 4) double or triple bonds in the chain.

Aryl denotes a phenyl radical or an ortho-fused bicyclic carbocyclic radical wherein at least one ring is aromatic. Het is a four-(4), five-(5), six-(6), or seven-(7) membered saturated or unsaturated ring containing 1, 2 or 3 heteroatoms selected from the group consisting of non-peroxide oxygen, sulfur, and nitrogen, which is optionally fused to a benzene ring, or any bicyclic heterocyclic group. Het includes "heteroaryl", which encompasses a radical attached via a ring carbon of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula (I) having any combination of the values, specific values, more specific values, and preferred values described herein. Mammal denotes human and animals, specifically including food animals and companion animals.

2. The Invention

The present invention comprises compounds of formula (1) as defined above, and their pharmaceutically acceptable salts.

For the compounds of formula (1), alkyl can be methyl, ethyl, propyl, isopropyl, butyl, iso-butyl, sec-butyl, pentyl, 3-pentyl, hexyl, heptyl, etc.; $C_{3-8}$ cycloalkyl can be cyclopropyl, cyclobutyl, cyclopentyl, cyclohexyl, cycloheptyl, or cyclooctyl; alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; het can be azetidinyl, 3,3-dihydroxy-1-azetinyl, pyrrolidino, piperidino, morpholino, thiomorpholino, or heteroaryl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

When alkyl is partially unsaturated, it can be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

In preferred embodiments either R2 or R4 or both R2 and R do not represent H.

In other preferred embodiments R2 is $C_{1-7}$ alkyl which may be partially unsaturated (although more preferably fully saturated) and optionally substituted by one or more substituents of the group $R^{10}$, $NR^7R^8$, halo, (C=O)$R^6$, or S(O)$_m R^6$, or $R^2$ is het, wherein said het is bound via a carbon atom.

Particularly preferred compounds are those where $R^2$ is 4-morpholinylmethyl, 3-hydroxypropyl, 3-hydroxy-1-propynyl or tetrahydro-2H-pyran-4-ylmethyl. In yet other preferred embodiments, X is Cl. Specifically preferred compounds include, but are not limited to the following:

N-(4-chlorobenzyl)-6-(4-morpholinylmethyl)-4-oxo-1-phenyl-1,4-dihydro-3-quinolinecarboxamide;

N-(4-chlorobenzyl)-6-(3-hydroxypropyl)-4-oxo-1-phenyl-1,4-dihydro-3-quinoline-carboxamide;

N-(4-chlorobenzyl)-6-(3-hydroxy-1-propynyl)-4-oxo-1-phenyl-1,4-dihydro-3-quinolinecarboxamide;

N-(4-chlorobenzyl)-4-oxo-1-phenyl-6-(tetrahydro-2H-pyran-4-ylmethyl)-1,4-dihydro-3-quinolinecarboxamide;

N-(4-chlorobenzyl)-1-(2-methylphenyl)-6-(4-morpholinylmethyl)-4-oxo-1,4-dihydro-3-quinolinecarboxamide;

N-(4-chlorobenzyl)-1-(3-iodophenyl)-6-(4-morpholinylmethyl)-4-oxo-1,4-dihydro-3-quinolinecarboxamide;

N-(4-chlorobenzyl)-1-(4-chlorophenyl)-6-(4-morpholinylmethyl)-4-oxo-1,4-dihydro-3-quinolinecarboxamide N-(4-chlorobenzyl)-1-(4-isopropylphenyl)-6-(4-morpholinylmethyl)-4-oxo-1,4-dihydro-3-quinolinecarboxamide;

N-(4-chlorobenzyl)-1-(4-methoxyphenyl)-6-(4-morpholinylmethyl)-4-oxo-1,4-dihydro-3-quinolinecarboxamide N-(4-fluorobenzyl)-1-(4-chlorophenyl)-6-(4-morpholinylmethyl)-4-oxo-1,4-dihydro-3-quinolinecarboxamide;

N-(4-chlorobenzyl)-6-(4-morpholinylmethyl)-4-oxo-1-(2,4-difluorophenyl)-1,4-dihydro-3-quinolinecarboxamide;

N-(4-chlorobenzyl)-6-(3-hydroxypropyl)-4-oxo-1-(2,4-difluorophenyl)-1,4-dihydro-3-quinolinecarboxamide;

N-(4-chlorobenzyl)-6-(3-hydroxy-1-propynyl)-4-oxo-1-(2,4-difluorophenyl)-1,4-dihydro-3-quinolinecarboxarnide;

N-(4-chlorobenzyl)-4-oxo-1-(2,4-difluorophenyl)-6-(tetrahydro-2H-pyran-4-yl-methyl)-1,4-dihydro-3-quinolinecarboxamide;

N-(4-Chlorobenzyl)-1-(2-(hydroxymethyl)phenyl)-6-(4-morpholinylmethyl)-4-oxo-1,4-dihydro-3-quinolinecarboxamide N-(4-Chlorobenzyl)-1-(2,3-dihydro-1H-inden-5-yl)-6-(4-morpholinylmethyl)-4-oxo-1,4-dihydro-3-quinolinecarboxamide; 1-(1,3-Benzodioxol-5-yl)-N-(4-chlorobenzyl)-6-(4-morpholinylmethyl)-4-oxo-1,4-dihydro-3-quinolinecarboxamide N-(4-Chlorobenzyl)-1-(1H-indol-5-yl)-6-(4-morpholinylmethyl)-4-oxo-1,4-dihydro-3-quinolinecarboxamide;

N-(4-Fluorobenzyl)-1-(1H-indol-5-yl)-6-(4-morpholinylmethyl)-4-oxo-1,4-dihydro-3-quinolinecarboxamide N-(4-Chlorobenzyl)-1-(3-hydroxyphenyl)-6-(4-morpholinylmethyl)-4-oxo-1,4-dihydro-3-quinolinecarboxamide N-(4-Chlorobenzyl)-1-(3-(2-hydroxyethyl)phenyl)-6-(4-morpholinylmethyl)-4-oxo-1,4-dihydro-3-quinolinecarboxamide;

N-(4-Fluorobenzyl)-1-(3-(2-hydroxyethyl)phenyl)-6-(4-morpholinylmethyl)-4-oxo-1,4-dihydro-3-quinolinecarboxarnide;

N-(4-chlorobenzyl)-1-(3-methoxyphenyl)-6-(4-morpholinylmethyl)4-oxo-1,4-dihydro-3-quinolinecarboxamide;

N-(4-chlorobenzyl)-1-(3-(hydroxymethyl)phenyl)-6-(4-morpholinylmethyl)-4-oxo-1,4-dihydro-3-quinolinecarboxamide N-(4-chlorobenzyl)-6-(4-morpholinylmethyl)-1-(4-(4-morpholinyl)phenyl)-4-oxo-1,4-dihydro-3-quinolinecarboxamide;

N-(4-chlorobenzyl)-1-(3,4-difluorophenyl)-6-(4-morpholinylmethyl)-4-oxo-1,4-dihydro-3-quinolinecarboxamide;

N-(4-chlorobenzyl)-1-(3-(3-hydroxy-1-propynyl)phenyl)-6-(4-morpholinylmethyl)-4-oxo-1,4-dihydro-3-quinolinecarboxamide;

N-(4-chlorobenzyl)-1-(3-(4-hydroxy-I-butynyl)phenyl)-6-(4-morpholinylmethyl)-4-oxo-1,4-dihydro-3-quinolinecarboxamide N-(4-chlorobenzyl)-1-(3-(4-hydroxy-I-butynyl)phenyl)-6-(4-morpholinylmethyl)-4-oxo-1,4-dihydro-3-quinolinecarboxamide N-(4-chlorobenzyl)-1-(3-(5-hydroxypentyl)phenyl)-6-(4-morpholinylmethyl)-4-oxo-1,4-dihydro-3-quinolinecarboxamide;

N-(4-chlorobenzyl)-1-(3-(4-hydroxybutyl)phenyl)-6-(4-morpholinylmethyl)-4-oxo-1,4-dihydro-3-quinolinecarboxamide N-(4-chlorobenzyl)-1-[3-(3-hydroxypropyl)phenyl]-6-(4-morpholinylmethyl)-4-oxo-1,4-dihydro-3-quinolinecarboxamide;

and pharmaceutically acceptable salts thereof.

The following Charts A–K describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts or by procedures analogous thereto, which would be well known to one of ordinary skill in organic chemistry. All of the variables used in the charts are as defined below or as in the claims.

Described examples and 1-aryl-4-oxo-dihydroquinoline intermediates are prepared through intramolecular ring cyclization of an enamine to an electron deficient haloarene (Wentland, M. P. et. al. *J. Med. Chem.* 1993, 36, 1580–1596), Chart A.

Most commonly the haloarene is a fluoroarene, though chloroarenes may also be employed, and the cyclization precursors may be prepared from properly substituted 3-(2-fluorophenyl)-3-oxo-propanoate esters (A.1). Specific examples of esters A.1 are prepared as described in Chart B (W=morpholinylmethyl), Chart C (W=iodo), Chart D (W=4-tetrahydropyranylmethyl), or Chart E (tert-butyldimethylsilyloxymethyl). Condensation of A.1 with triethylorthoformate in acetic anhydride at 150° C. affords the enol ether A.2 which can be further condensed with aniline or a substituted aniline in an alcohol solvent to afford the enamine A.3. Ring cyclization is affected by treating A.3 with an appropriate base such as sodium hydride, potassium tert-butoxide, or potassium carbonate in an aprotic solvent such as tetrahydrofuran, dioxane, or dimethylformamide to provide quinoline derivatives of the formula A.4.

The resulting ester A.4 is then treated with a benzylamine (e.g. 4-chlorobenzylamine, 4-bromobenzylamine, or 4-fluorobenzylamine) at high temperature to afford the corresponding amides of the general formula A.5 or ester A.4 is saponified to afford the corresponding acid which is then coupled with a benzylamine to likewise provide amides of the general formula A.5.

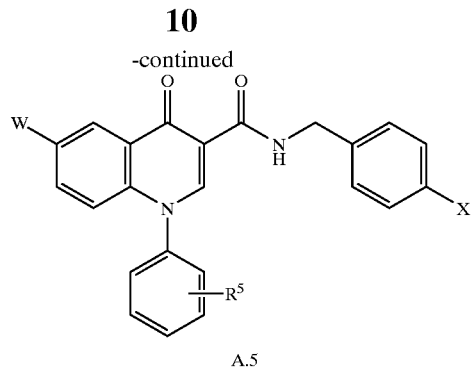

A.5

A.1 (W=morpholinylmethyl) is prepared according to Chart B. Reductive amination of 3-bromo-4-fluorobenzaldehyde (B.1) with morpholine, acetic acid, and sodium triacetoxyborohydride provides the benzylmorpholine B.2. Metal-halogen exchange between n-butyllithium and B.2 at −70° C. in tetrahydrofuran followed by addition of the resulting aryllithium to N-methoxy-N-methylacetamide yields the methylketone B.3. Treatment of B.3 with a base such as sodium hydride in the presence diethylcarbonate affords the 3-ketoester B.4 which may then be employed as in Chart A.

A.1 (W=iodo) is prepared according to Chart C. Lithiation of 4-iodo-fluorobenzene (C.1) with lithium diusopropylamine at −70° C. in tetrahydrofuran followed by quenching with carbon dioxide (Blackburn, B. K. et. al. *J. Med. Chem.* 1997, 40, 717–729) provides 2-fluoro-5-iodobenzoic acid (C.2). Conversion of C.2 to its corresponding imidazolide with 1,1'-carbonyldiumidazole followed by treatment with the trimethylsilyl ester of ethyl hydrogen malonate in the presence of DBU (Wang, X.; Monte, W. T.; Napier, J. J.; Ghannam, A. *Tetrahedron Lett.* 1994, 35, 9323–9326) provides 3-ketoester C.3 which may be employed as in Chart A.

CHART A

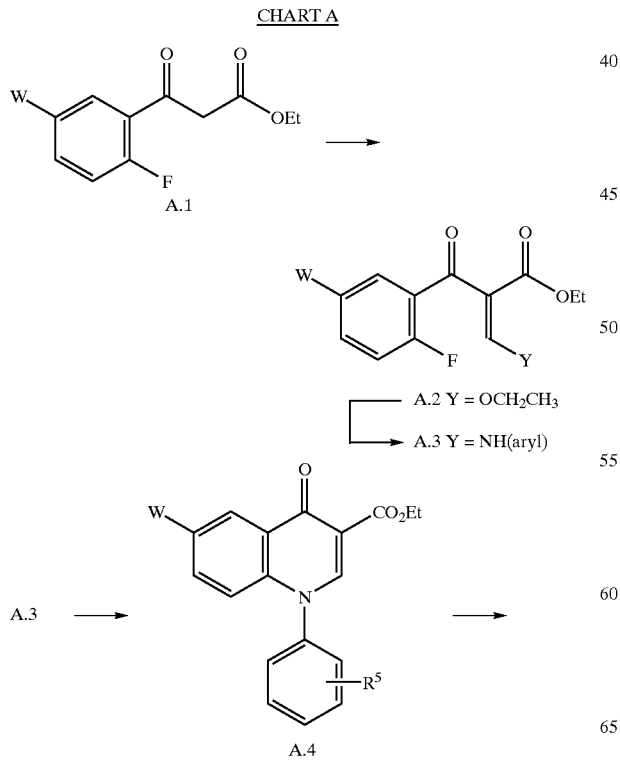

CHART B

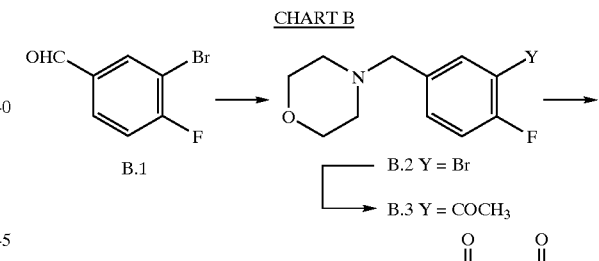

CHART C

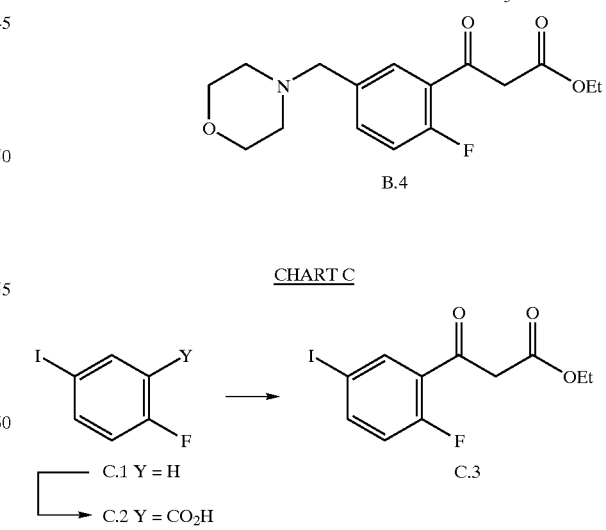

A.1 (W=4-tetrahydropyranylmethyl) is prepared according to Chart D. Wittig olefination between 3-bromo-4- fluorobenzaldehyde (B.1) and 4-tetrahydro-pyranylphosphonium bromide (Bestmann, H. J.; Stransky, W.; Vostrowsky, 0. *Chem. Ber.* 1979, 109, 1694–1700.) employing sodium hexamethyldisilazide as base provides the olefin D.1. Metal-halogen exchange between n-butyllithium and D.1 at -70° C. in tetrahydrofuran followed by addition of the resulting aryllithium to carbon dioxide yields the carboxylic acid D.2. Saturation of the olefin by hydrogenation of D.2 employing palladium on carbon as catalyst affords D.3. Conversion of D.3 to its corresponding imidazolide with 1,1'-carbonyldiimidazole followed by treatment with the trimethylsilyl ester of ethyl hydrogen malonate in the presence of DBU (Wang, X.; Monte, W. T.; Napier, J. J.; Ghannam, A. *Tetrahedron Lett.* 1994, 35, 9323–9326) provides 3-ketoester D.4 which may be employed as in Chart A.

A.1 (W=tert-butyldimethylsilyloxymethyl) is prepared according to Chart E. Reduction of 3-bromo-4-fluorobenzaldehyde (B.1) with sodium borohydride in ethanol provides the corresponding benzyl alcohol E.1. The resulting alcohol is silylated employing tert-butyldimethylsilylchloride and imidazole in DMF to afford silylether E.2. Metal-halogen exchange between n-butyllithium and E.2 at -70° C. in tetrahydrofuran followed by addition of the resulting aryllithium to carbon dioxide yields the carboxylic acid E.3. Conversion of E.3 to its corresponding imidazolide with 1,1'-carbonyldiimidazole followed by treatment with the trimethylsilyl ester of ethyl hydrogen malonate in the presence of DBU (Wang, X.; Monte, W. T.; Napier, J. J.; Ghannam, A. *Tetrahedron Lett.* 1994, 35, 9323–9326) provides 3-ketoester E.4 which may be employed as in Chart A.

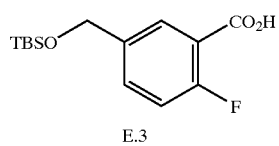

E.3

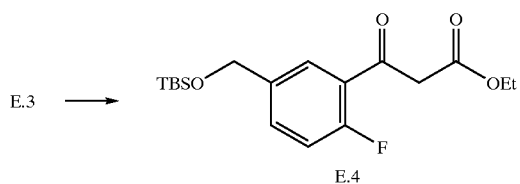

E.3 →

E.4

Where W=iodo, the products of Chart A (A.5, W=iodo) are further elaborated as described in Chart F. Sonogashira coupling of A.5 (W=iodo) with a variety of electron rich acetylenes (e.g. propargyl alcohol; Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula F.1. Saturation of the alkyne by hydrogenation catalyzed by palladium on carbon in alcoholic solvents affords alkyl derivatives of formula F.2. In addition, compounds of the form A.5 (W=I) undergo coupling reactions catalyzed by palladium reagents (e.g. Pd(OAc)$_2$, Pd(PPh$_3$)$_4$, PdCl$_2$(PPh$_3$)$_2$) including but not limited to (a) Suzuki couplings with boronic acids and esters, (b) Stille coupling with stannyl reagents, and (c) Heck coupling with alkenes to afford compounds of the formula F.3 (V=optionally substituted aryl, heteroaryl, or vinylic substituents). Similarly, compounds of the form A.5 (W=I) undergo palladium catalyzed carbon monoxide insertion in the presence of optionally substituted alcohols or amines to provide compounds of the formula F.4 (T=OR$^{11}$, NR$^7$R$^8$).

CHART D

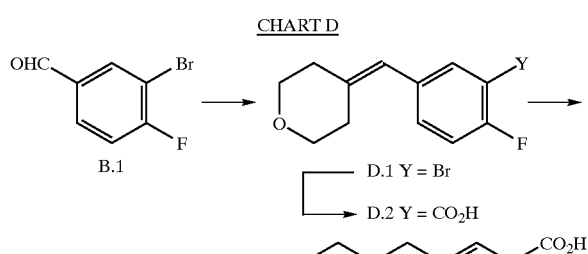

B.1 → D.1 Y = Br
→ D.2 Y = CO$_2$H

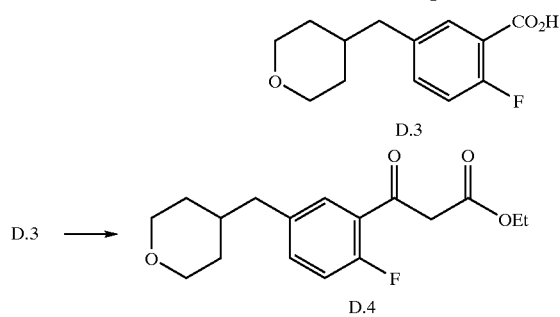

D.3

D.3 →

D.4

CHART E

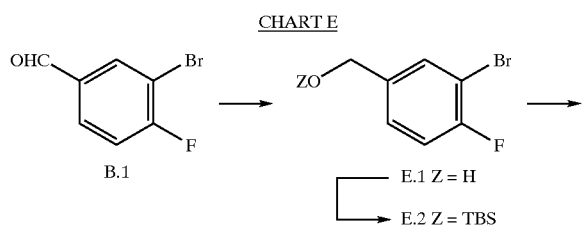

B.1 →
E.1 Z = H
→ E.2 Z = TBS

CHART F

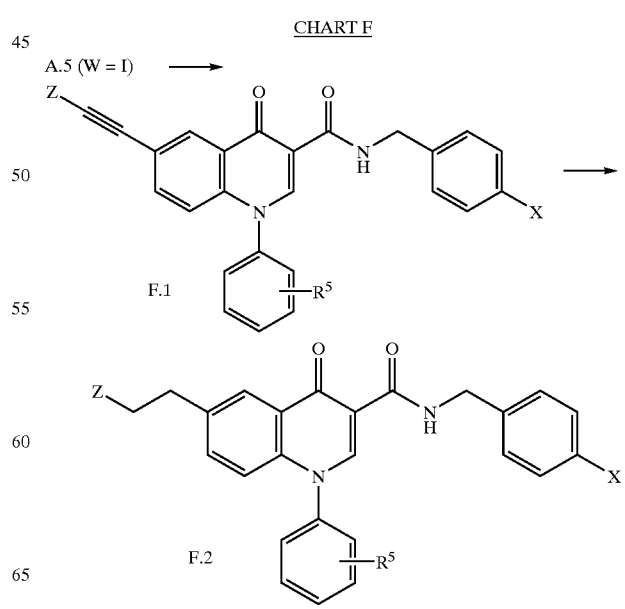

A.5 (W = I) →

F.1

F.2

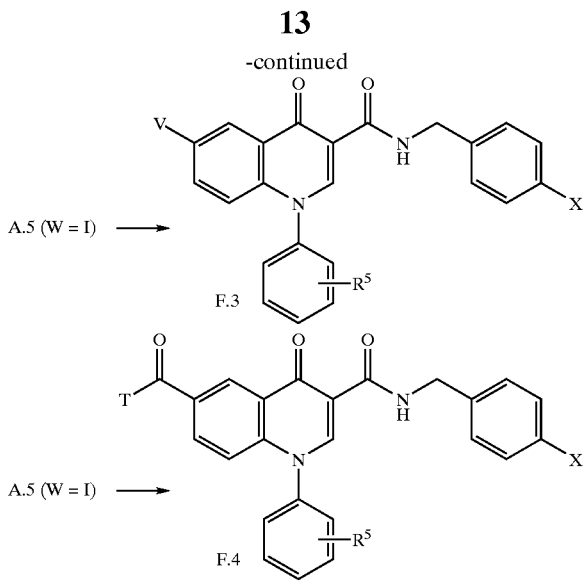

As described in Chart G, compounds of the formula A.5 (W=tertbutyldimethylsilyl or another suitable alcohol protecting group) prepared according to Chart A or similarly are deprotected under methods common to the literature (Green, T. W; Wuts, P. G. M. *Protective Groups in Organic Synthesis*. Wiley, 1999) to afford the alcohol G.1. Treatment of compound G.1 with methanesulfonyl chloride followed by displacement with an amine, HNR$^7$R$^8$ wherein R$^7$ and R$^8$ are the same as defined above, affords compounds of the structure described by Formula G.2.

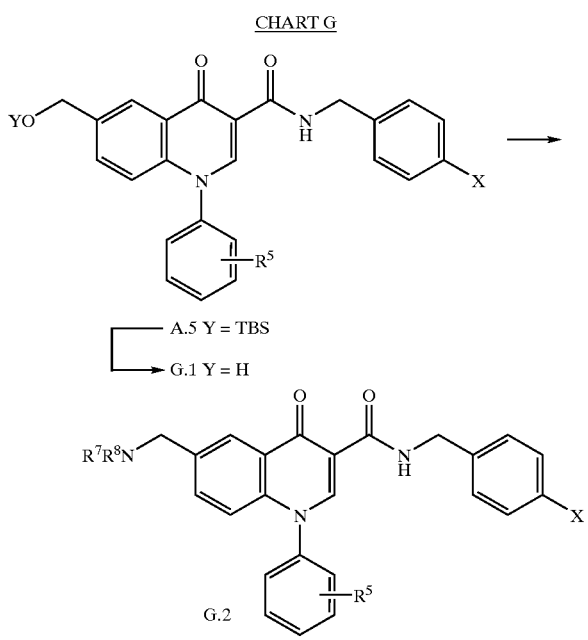

As described in Chart H, compounds of the general formula H.1 where the iodide substituent R$^5$ is attached to the aryl ring at either the ortho, meta, or para positions (W may be, but is not limited to, morpholinylmethyl, hydroxyalkyl, hydroxyalkynyl, aryl, or het) are further functionalized. Sonogashira coupling of H.1 with a variety of electron rich acetylenes (e.g. propargyl alcohol; Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula H.2. Partial saturation of the alkyne by Lindlar hydrogenation provides the corresponding (E)-or (Z)-alkenes H.3. Alternatively, hydrogenation catalyzed by palladium on carbon in alcoholic solvents affords alkyl derivatives of formula H.4.

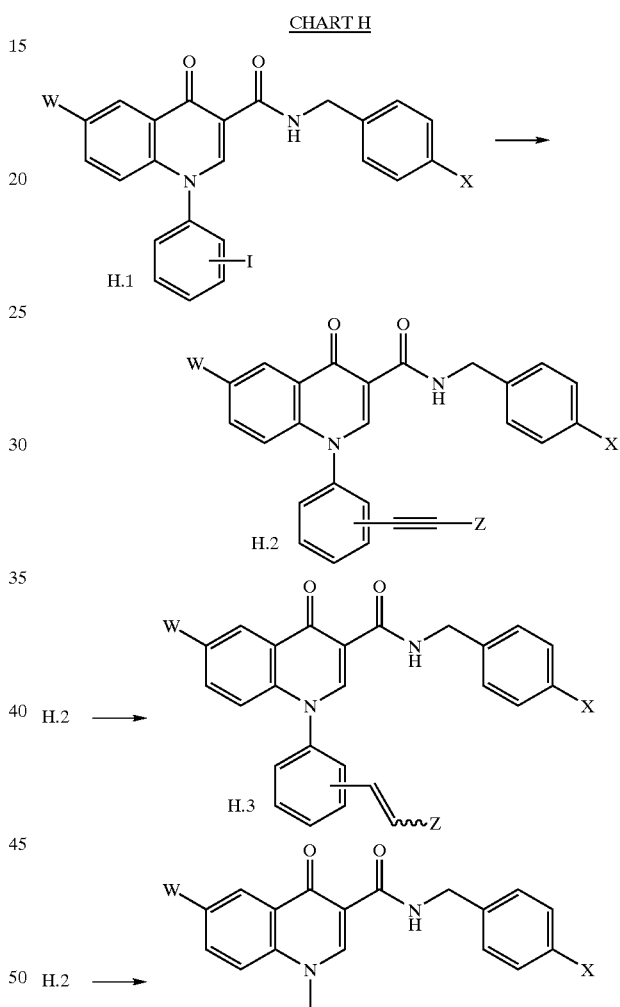

Compounds of general formula 1.1 prepared according to the above descriptions or analogous to them in which R$^5$=CH$_2$OH and is attached at either the ortho, meta, or para positions of the aryl ring are converted to the corresponding alkylamines as shown in Chart I. Treatment of compound 1.1 with methanesulfonyl chloride followed by displacement with an amine, HNR$^7$R$^8$ wherein R$^7$ and R$^8$ are the same as defined above, affords compounds of the structure described by Formula 1.2.

CHART I

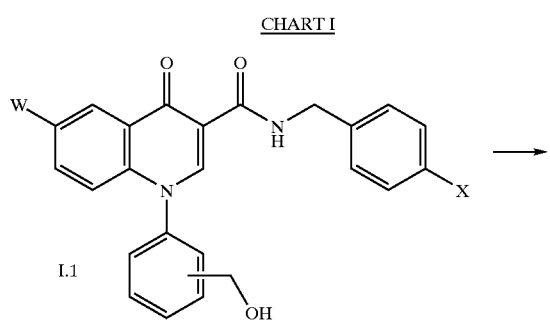

As shown in Chart J, compounds of the formula J.1 (n=1 or 2) are converted the corresponding imidazolide with 1,1'-carbonyldiimidazole and treated with the trimethylsilyl ester of ethyl hydrogen malonate in the presence of DBU (Wang, X.; Monte, W. T.; Napier, J. J.; Ghannam, A. Tetrahedron Lett. 1994, 35, 9323–9326) to provide 3-ketoester J.2. Condensation of J.2 with triethylorthoformate in acetic anhydride at 150° C. affords an intermediate enol ether which is further condensed with aniline or a substituted aniline in an alcohol solvent to afford the enamine J.3. Ring cyclization is affected by treating J.3 with an appropriate base such as sodium hydride, potassium tert-butoxide, or potassium carbonate in a solvent such as tetrahydrofuran, tert-butanol, dioxane, or dimethylformamide to provide quinoline derivatives of the formula J.4. The resulting ester J.4 is then treated with a benzylamine (e.g. 4-chlorobenzylamine, 4-bromobenzylamine, or 4-fluorobenzylamine) at high temperature to afford the corresponding amides of the general formula J.5 or ester J.4 is saponified to afford the corresponding acid which is then coupled with a benzylamine to likewise provide amides of the general formula J.5. Treatment of compound J.5 with methanesulfonyl chloride followed by displacement with an amine, $HNR^7R^8$ wherein $R^7$ and $R^8$ are the same as defined above, affords compounds of the structure described by Formula J.6.

CHART J

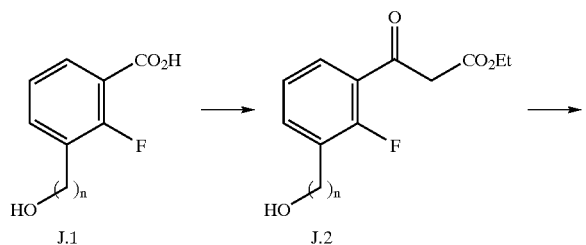

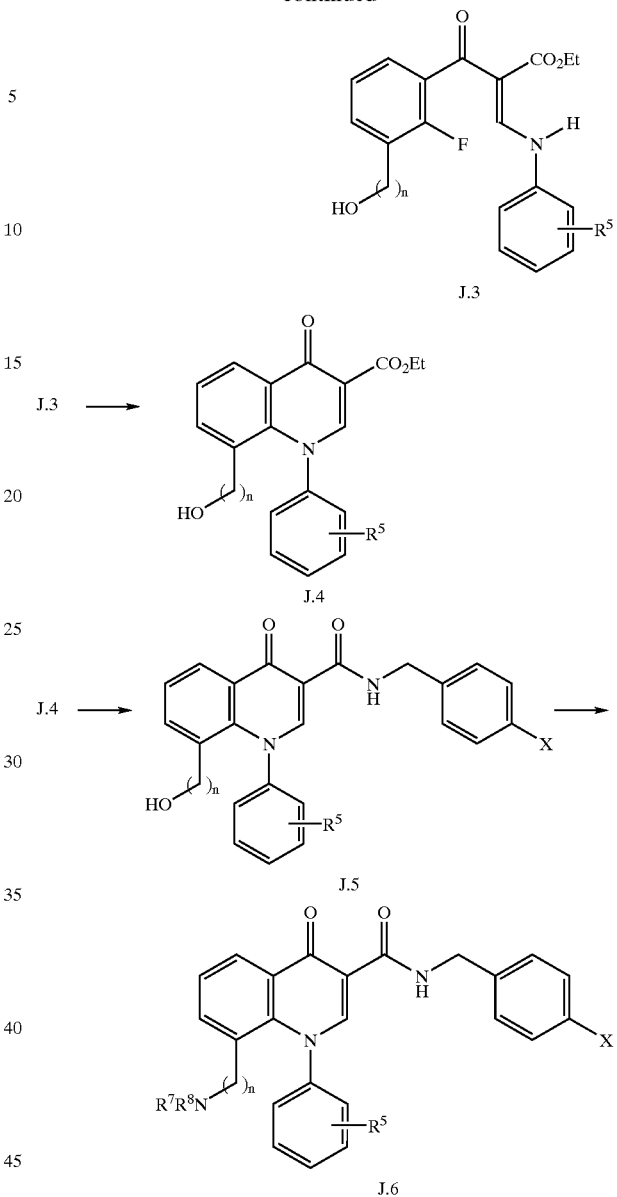

Additional $R^4$ substituents are incorporated as shown in Chart K. 1-Fluoro-2-iodobenzene (K.1) is metalated with lithium diisopropylamide at low temperature and then reacted with carbon dioxide according to a literature precedent (Moyround, J.; Guesnet, J.; Bennetau, B.; Mortier, J. Tetrahedron Lett. 1995, 36, 881–884.) to afford K.2. Carboxylic acid K.2 is converted to the corresponding imidazolide with 1,1'-carbonyldiimidazole and treated with the trimethylsilyl ester of ethyl hydrogen malonate in the presence of DBU to provide 3-ketoester K.3. Condensation of K.3 with triethylorthoformate in acetic anhydride at 150° C. affords an intermediate enol ether which is further condensed with aniline or a substituted aniline in an alcohol solvent to afford the enamine K.4. Ring cyclization is affected by treating K.4 with an appropriate base such as sodium hydride or potassium tert-butoxide in a solvent such as tetrahydrofuran, t-butanol, or dioxane to provide quinoline derivatives of the formula K.5. The resulting ester K.5 is then treated with a benzylamine (e.g. 4-chlorobenzylamine, 4-bromobenzylamine, or 4-fluorobenzylamine) at high temperature to afford the corresponding amides of the general formula K.6 or ester K.5 is saponified to afford the corresponding acid which is then coupled with a benzylamine to likewise provide amides of the general formula K.6. Sonogashira coupling of K.6 with a variety of electron rich acetylenes (e.g. propargyl alcohol; Z=CH$_2$OH) catalyzed by PdCl$_2$(PPh$_3$)$_2$ and copper(I) iodide either in diethylamine or in a mixture of DMF and triethylamine provides the corresponding alkynyl derivatives of formula K.7. Saturation of the alkyne through hydrogenation catalyzed by palladium on carbon in alcoholic solvents affords alkyl derivatives of formula K.8.

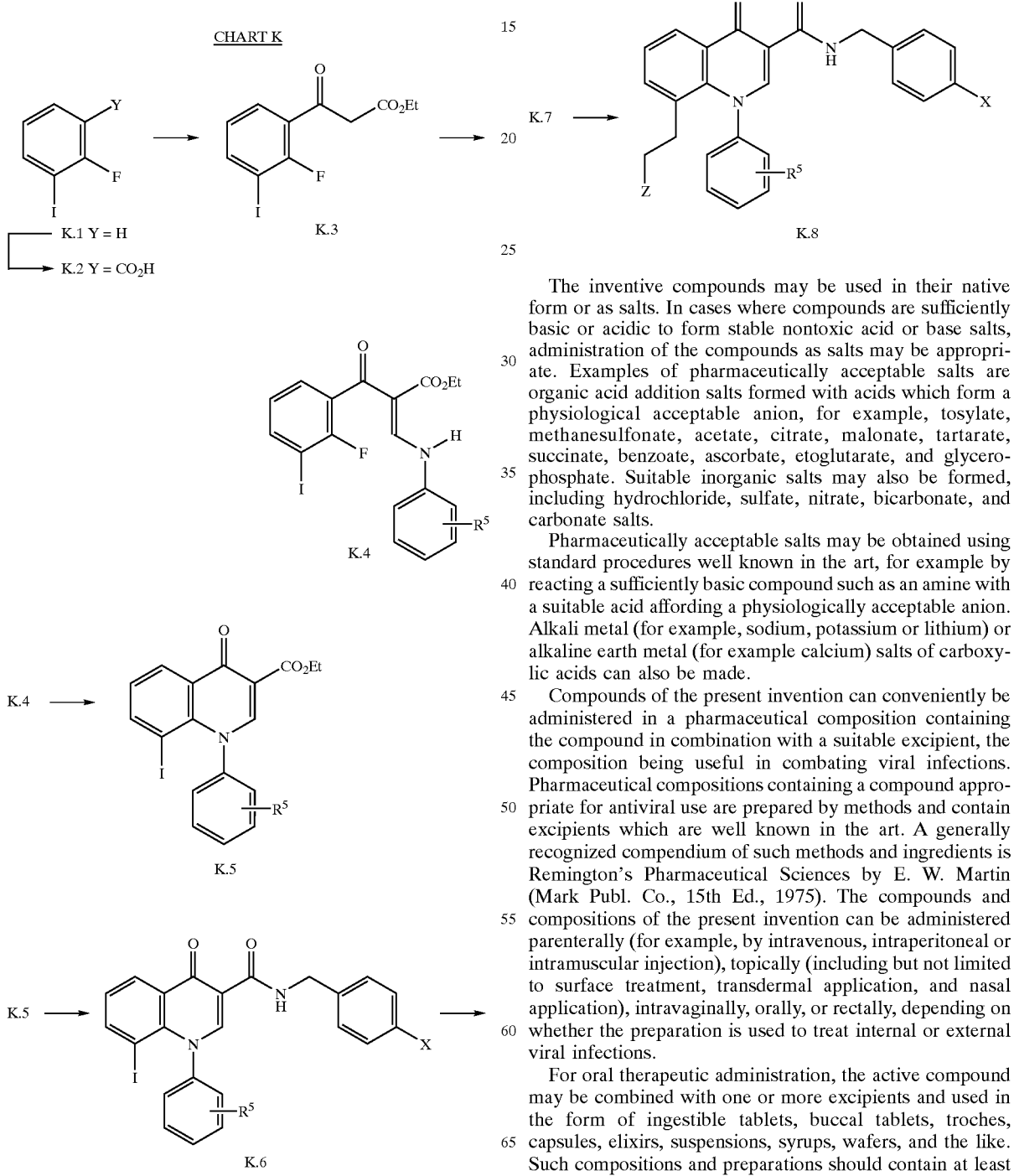

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, etoglutarate, and glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically (including but not limited to surface treatment, transdermal application, and nasal application), intravaginally, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices such as the osmotic release type devices developed by the Alza Corporation under the OROS trademark.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

The compounds of formula (I) and pharmaceutically acceptable salts thereof are useful as antiviral agents. Thus, they are useful to combat viral infections in mammals, including man. The compounds are generally active against herpes viruses, and are particularly useful against the varicella zoster virus, the Epstein-Barr Virus, the herpes simplex virus types 1 and 2 (HSV-1 and 2), the human herpes virus types 6, 7 and 8 (HHV-6, 7 and 8) and the human cytomegalovirus (HCMV).

The invention will be further described by the following non-limiting examples.

PREPARATION 1

4-(3-Bromo-4-fluorobenzyl)morpholine [B.2].

A solution of 3-bromo-4-fluorobenzaldehyde (50.0 g) in 1,2-dichloroethane (500 mL) is cooled to 0° C. Acetic acid (14.1 mL) and morpholine (23.6 mL) are added slowly, maintaining the temperature below 4° C. Sodium triacetoxyborohydride (78.3 g) is added all at once, maintaining the temperature below 5° C. The mixture is allowed to warm to rt and stirred for 18 hrs. The reaction is quenched with 1 N NaOH (200 mL) and extracted with $CH_2Cl_2$ (500 mL). The organic layer is washed with 1 N NaOH (2×200 mL). The aqueous layers are combined and back-extracted with $CH_2Cl_2$ (100 mL). The organic layers are combined and extracted with 0.5 N HCl (5×250 mL). The acidic aqueous layers are combined, and 2 N NaOH is added until the solution is basic (pH=12). The aqueous layer is then extracted with $CH_2Cl_2$ (6×100 mL). The organic layers are combined, dried ($MgSO_4$) and concentrated in vacuo to a clear, colorless oil. The crude product is distilled (126° C., 0.3 Torr) to afford 48.9 g (72%) of the title compound as a clear, colorless oil. Physical characteristics: B.p. 126° C. (0.3 Torr); $^1H$ NMR (300 MHz, DMSO-$d_6$) δ 7.62, 7.35–7.29, 3.56, 3.45, 2.34; $^{13}C$ NMR (75 MHz, DMSO-$d_6$) δ 157.3, 136.1, 133.3, 129.8, 116.2, 107.7, 66.1, 60.9, 53.0; IR (liq.) 2855, 2807, 1495, 1455, 1348, 1257, 1244, 1118, 1009, 862 cm$^{-1}$; MS (ESI+) m/z 274 (M+H)$^+$. Anal. Calcd for $C_{11}H_{13}BrFNO$: C, 48.20; H, 4.78; N, 5.11; Br, 29.15. Found: C, 48.04; H, 4.79; N, 5.11; Br, 28.18.

PREPARATION 2

1-(2-Fluoro-5-(4-morpholinylmethyl)phenyl)ethanone [B.3].

4-(3-Bromo-4-fluorobenzyl)morpholine (Preparation 1, 35.5 g) is dissolved in THF (400 mL) and cooled to −75° C. A solution of n-butyllithium in hexane (2.5 M, 57.0 mL) is added via addition funnel, maintaining the temperature below −68° C. A solution of N-methoxy-N-methylacetamide (16.0 g) in THF (50 mL) is added via addition funnel, maintaining the temperature below −65° C. The reaction is stirred at −75° C. for 1 h and allowed to warm to rt overnight. The reaction is quenched with 1 N HCl (150 mL) and poured into ethyl acetate (400 mL). The aqueous layer is separated, made basic with sat. aq. $NaHCO_3$, and extracted with ethyl acetate (2×100 mL). The combined organic layers are washed with sat. $NaHCO_3$ (2×100 mL) and brine (50 mL). The combined aqueous washes are back-extracted with ethyl acetate (100 mL). The organic layers are combined, dried ($Na_2SO_4$), and concentrated in vacuo to a yellow oil. The crude product is distilled (135° C., 0.3 Torr) to afford 19.7 g (64%) of the title compound as a clear, colorless oil. Physical characteristics: B.p. 135° C. (0.3 Torr); $^1H$ NMR (300 MHz, DMSO-$d_6$) δ 7.72, 7.61–7.56, 7.31, 3.56, 3.48, 2.58, 2.34; IR (liq.) 1996, 1979, 1919, 1688, 1612, 1492, 1417, 1361, 1291, 1281, 1212, 1118, 865 cm$^{-1}$; MS (ESI+) m/z 238 (M+H)$^+$. Anal. Calcd for $C_{13}H_{16}FNO_2$: C, 65.81; H, 6.80; N, 5.90. Found: C, 65.43; H, 6.75; N, 5.84.

PREPARATION 3

Ethyl 3-(2-fluoro-5-(4-morpholinylmethyl)phenyl)-3-oxopropanoate [B.4]

Sodium hydride (60% dispersion in mineral oil, 6.6 g) is slowly added to a solution of 1-(2-fluoro-5-(4-morpholinylmethyl)phenyl)ethanone (Preparation 2, 19.6 g) in diethyl carbonate at 0° C. The mixture is stirred at 0° C. for 1 h and allowed to warm to rt overnight. The reaction is quenched with acetic acid (10 mL), diluted with water (200 mL) and made basic with sat. aq. $Na_2CO_3$. The mixture is extracted with diethyl ether (3×200 mL). The combined organic layers are washed with sat. $NaHCO_3$ (100 mL) and brine (50 mL). The combined aqueous layers are back-extracted with diethyl ether (50 mL). The organic layers are combined, dried ($Na_2SO_4$) and concentrated in vacuo to an orange oil. The crude product is purified by column chromatography (heptane/IPA, 8/1; 4/1; $CH_2Cl_2$/MeOH, 98/2) to afford 20.2 g (79%) of the compound as a yellow oil. Physical characteristics: $^1H$ NMR (300 MHz, DMSO-$d_6$) δ 7.78, 7.65–7.60, 7.32, 4.10, 4.05, 3.57, 3.50, 2.34, 1.16; IR (liq.) 1996, 1979, 1744, 1689, 1626, 1611, 1493, 1331, 1260, 1215, 1147, 1117, 865 cm$^{-1}$; MS (ESI+) m/z 310 (M+H)$^+$. Anal. Calcd for $C_{16}H_{20}FNO_4$: C, 62.12; H, 6.52; N, 4.53. Found: C, 61.96; H, 6.67; N, 4.44.

PREPARATION 4

Ethyl 3-ethoxy-2-(2-fluoro-5-(4-morpholinylmethyl)benzoyl)-2-propenoate [A.2, W=morpholinylmethyl].

A mixture of ethyl 3-(2-fluoro-5-(4-morpholinylmethyl)phenyl)-3-oxopropanoate (Preparation 3, 20.0 g), triethylorthoformate (21.5 ML) and acetic anhydride (21.4 mL) is heated at 150° C. in a round-bottom flask equipped with a Dean-Stark trap and condenser. After 4 h, the remaining acetic acid and triethylorthoforrnate are distilled off by heating the mixture to 100° C. at 0.2 Torr for 1 hr, leaving 22.9 g of the title compound as an amber oil. The crude product is used as is in the subsequent transformations. Physical characteristics: $^1H$ NMR (300 MHz, DMSO-$d_6$) δ 7.85, 7.60–7.45, 7.23, 4.36–4.17, 4.09–3.99, 3.56, 3.49, 2.34, 1.29–1.11, 1.08–0.99; MS (ESI+) m/z 366 (M+H)$^+$.

General Preparation A.3. A corresponding aniline ($H_2N$ (aryl), 1.5 equiv) is added to a solution of ethyl 3-ethoxy-2-(2-fluoro-5-(4-morpholinylmethyl)benzoyl)-2-propenoate (Preparation 4) in ethanol (0.5 M). The mixture is stirred at a prescribed temperature for a period of 18–24 h and is then concentrated in vacuo to afford an oil. The crude product is purified by column chromatography or recrystallization to afford the desired intermediate A.3. The following compounds (Preparations 5a–5p) are prepared according to these procedures.

PREPARATION 5a

Ethyl 3-anilino-2-(2-fluoro-5-(4-morpholinylmethyl) benzoyl)-2-propenoate [A.3, W=morpholinylmethyl, aryl=phenyl]

Condensation of aniline (0.47 mL) according to the general procedure at 50° C. for 18 h followed by purification by column chromatography ($CH_2Cl_2$/MeOH, 99/1; 98/2) affords 1.01 g (89%) of the title compound as a yellow oil. Physical characteristics: $^1H$ NMR (300 MHz, DMSO-$d_6$) δ 12.22, 10.85, 8.51, 8.39, 7.51–7.10, 4.01–3.93, 3.59–3.52, 3.48, 2.37–2.33, 0.94, 0.82; IR (liq.) 1700, 1671, 1626, 1598, 1570, 1428, 1301, 1280, 1254, 1215, 1200, 1117 $cm^{-1}$; MS (ESI+) m/z 413 (M+H)$^+$; HRMS (FAB) calcd for $C_{23}H_{25}FN_2O_4$+H m/z 413.1876, found 413.1880.

PREPARATION 5b

Ethyl 2-(2-Fluoro-5-(4-morpholinylmethyl)benzoyl)-3-(2-toluidino)-2-propenoate [A.3, W=morpholinylmethyl, aryl=2-methylphenyl]

Condensation of o-toluidine (0.44 mL) according to the general procedure at rt for 24 h followed by purification by column chromatography ($CH_2Cl_2$/MeOH, 99/1; 97.5/2.5) affords 1.05 g (91%) of the title compound as a yellow oil. Physical characteristics: $^1H$ NMR (300 MHz, DMSO-$d_6$) δ 12.63, 11.00, 8.59, 8.46, 7.62, 7.52, 7.45–7.12, 3.96, 3.57, 3.48, 2.39–2.32, 0.96, 0.82; IR (liq.) 1704, 1625, 1604, 1592, 1572, 1429, 1307, 1281, 1254, 1227, 1211, 1118 $cm^{-1}$; MS (ESI+)⁻m/z 427 (M+H)$^+$; HRMS (FAB) calcd for $C_{24}H_{27}FN_2O_4$+H m/z 427.2033, found 427.2024.

PREPARATION 5c

Ethyl 2-[2-fluoro-5-(4-morpholinylmethyl)benzoyl]-3-(3-iodoanilino)-2-propenoate [A.3, W=morpholinylmethyl, aryl=3-iodophenyl Condensation with 3-iodoaniline (1.09 mL) according to the general procedure at 50° C. for 18 h followed by recrystallization from ethanol affords 4.046 g (90%) of the title compound as a tan solid. Physical characteristics: M.p. 128–131° C.; $^1H$ NMR (300 MHz, DMSO-$d_6$) δ 12.05, 10.75, 8.475, 8.33, 7.92, 7.59–7.32, 7.24–7.11, 3.95, 3.57, 3.48, 2.35, 0.93, 0.82; $^{13}C$ NMR (75 MHz, CDCl$_3$) δ 192.2, 189.3, 168.9, 151.9, 151.3, 140.5, 140.4, 135.2, 134.6, 134.1, 133.0, 132.9, 131.7, 131.6, 130.8, 129.8, 127, 1, 126.6, 117.7, 117.1, 115.5, 115.3, 106.0, 95.4, 67.4, 62.8, 60.7, 60.4, 53.9, 14.3, 13.8; IR (drift) 1693, 1663, 1615, 1583, 1560, 1295, 1278, 1271, 1261, 1255, 1241, 1232, 1214, 1110, 769 cm; MS (ESI+) m/z 539 (M+H)$^+$. Anal. Calcd for $C_{23}H_{24}FIN_2O_4$: C, 51.31; H, 4.49; N, 5.20; F, 3.53. Found: C, 51.30; H, 4.52; N, 5.14.

PREPARATION 5d

Ethyl-3-(4-chloroanilino)-2-[2-fluoro-5-(4-morpholinylmethyl)benzoyl]-2-propenoate [A.3, W=morpholinylmethyl, aryl=4-chlorophenyl.

Condensation with 4-chloroaniline (1.14 mL) according to the general procedure at 50 C for 18 h followed by recrystallization from ethanol affords 2.62 g (73%) of the title compound as a yellow solid. Physical characteristics: $^1H$ NMR (300 MHz, DMSO-$d_6$) δ 12.12, 10.82, 8.45, 8.32, 7.58–7.32, 7.15, 3.95, 3.57, 3.48, 2.35, 0.94, 0.82; IR (drift) 1692, 1663, 1638, 1615, 1594, 1568, 1440, 1303, 1294, 1278, 1253, 1231, 1219, 1201, 1109 $cm^{-1}$; MS (ESI+) m/z 447 (M+H)$^+$. Anal. Calcd for $C_{23}H_{24}ClFN_2O_4$: C, 61.81; H, 5.41; N, 6.27; Cl, 7.93; F, 4.25. Found: C, 61.67; H, 5.40; N, 6.24; Cl, 7.87.

PREPARATION 5e

Ethyl-2-[2-fluoro-5-(4-morpholinylmethyl)benzoyl]-3-(4-isopropylanilino)-2-propenoate [A.3, W=morpholinylmethyl, aryl=4-isopropylphenyl Condensation of 4-isopropylaniline (1.22 mL) according to the general procedure at 50° C. for 18 h followed by purification by column chromatography ($CH_2Cl_2$/methanol, 99/1; 98/2) affords 3.34 g (99%) of the title compound as an orange oil. Physical characteristics: $^1H$ NMR (300 MHz, DMSO-$d_6$) δ 12.28, 10.85, 8.48, 8.37, 7.45–7.30, 7.14, 3.94, 3.57, 3.48, 2.91, 2.35, 1.22–1.18, 1.09, 0.93, 0.82; $^{13}C$ NMR (75 MHz, CDCl$_3$) o 152.8, 147.4, 128.3, 128.2, 118.4, 117.9, 115.2, 67.4, 62.8, 60.4, 53.9, 34.0, 24.3, 14.3; IR (liq.) 2961, 1698, 1670, 1627, 1608, 1566, 1438, 1424, 1305, 1280, 1253, 1217, 1205, 1118, 1101 $cm^{-1}$; MS (ESI+) m/z 445 (M+H)+. HRMS (FAB) calcd for $C_{26}H_3$,$FN_2O_4$+H m/z 455.2346, found 455.2364.

PREPARATION 5f

Ethyl 2-[2-fluoro-5-(4-morpholinylmethyl)benzoyl]-3-(4-methoxyanilino)-2-propenoate [A.3, W=morpholinylmethyl, aryl=4-methoxyphenyl.

Condensation of 4-methoxyaniline (1.10 g) according to the general procedure at 60° C. for 18 h followed by purification by column chromatography ($CH_2Cl_2$/MeOH, 99/1; 98/2) affords 2.268 g (74%) of the title compound as a yellow oil. Physical characteristics: $^1H$ NMR (300 MHz, DMSO-$d_6$) δ 12.34, 10.85, 8.42, 8.31, 7.47, 7.44–7.33, 7.30, 7.19–7.10, 7.05–6.95, 3.96, 3.77, 3.57, 3.48, 2.35, 0.93, 0.81; $^3C$ NMR (75 MHz, CDCl$_3$) o 167.4, 158.3, 158.0, 153.1, 152.8, 133.9, 132.7, 132.5, 132.0, 129.7, 1119.9, 119.5, 115.5, 115.4, 115.2, 103.9, 67.4, 62.8, 62.7, 60.4, 60.1, 56.0, 53.9, 14.3, 13.9; IR (mull) 1689, 1667, 1625, 1612, 1562, 1518, 1423, 1308, 1281, 1262, 1252, 1231, 1208, 1179, 1110 $cm^{-1}$; MS (ESI+) m/z 443 (M+H)$^+$; HRMS (FAB) calcd for $C_{24}H_{27}FN_2O_5$+H m/z 443.1982, found 443.1984.

PREPARATION 5g

Ethyl 2-(2-Fluoro-5-(4-morpholinylmethyl)benzoyl)-3-(2-(hydroxymethyl)anilino)-2-propenoate [A.3, W=morpholinylmethyl, aryl=2-hydroxymethylphenyl.

Condensation with 2-aminobenzyl alcohol (1.12 g) according to the general procedure at room temperature for 66 h followed by purification by column chromatography ($CH_2Cl_2$/methanol, 100/1; 50/1; 33/1) affords 2.91 g (80%) of the title compound as a light yellow amorphous solid. Physical characteristics: $^1H$ NMR (300 MHz, DMSO-$d_6$) δ 12.74, 11.48, 8.49, 8.40, 7.61–7.11, 5.74–5.68, 4.62, 4.01–3.92, 3.58, 3.48, 2.35, 0.95, 0.84; IR (diffuse reflectance) 1695, 1680, 1627 (s), 1608 (b), 1591 (s), 1563 (s), 1429, 1304 (s), 1279 (s), 1254 (s), 1210, 1188, 1116, 1104, 758 $cm^{-1}$; MS (ESI+) m/z 443 (100, M+H)$^+$), 444 (26); HRMS calcd for $C_{24}H_{27}FN_2O_5$+H m/z 443.1982, found 443.1986.

PREPARATION 5h

Ethyl 3-(2,3-Dihydro-1H-inden-5-ylamino)-2-(2-fluoro-5-(4-morpholinylmethyl)-benzoyl)-2-propenoate [A.3, W=morpholinylmethyl, aryl=indan Condensation with 5-aminoindan (1.2 g) according to the general procedure at room temperature for 66 h followed by filtration affords 2.15 g (58%) of the title compound as a light yellow solid. Physical characteristics: M.p. 101–102° C.; $^1H$ NMR (400 MHz, DMSO-$d_6$) δ 12.33, 10.84, 8.50, 8.39, 7.44–7.12, 3.98–3.92, 3.57, 3.47, 2.92–2.83, 2.35, 2.08–2.00, 0.94, 0.81; IR (diffuse reflectance) 1692, 1662 (s), 1635, 1610 (s), 1598, 1569 (s), 1423, 1319 (s), 1306, 1292 (s), 1282 (s), 1253 (s), 1233, 1202 (s), 1110 (s) cm$^{-1}$; MS (ESI+) m/z 453 (100, M+H)$^+$), 454 (23). Anal. Calcd for $C_{26}H_{29}FN_2O_4$: C, 69.01; H, 6.46; N, 6.19; F, 4.20. Found: C, 69.03; H, 6.47; N, 6.20; F, 4.19.

PREPARATION 5i

Ethyl 3-(1,3-Benzodioxol-5-ylamino)-2-(2-fluoro-5-(4-morpholinylmethyl)benzoyl)-2-propenoate [A.3, W=morpholinylmethyl, aryl=3,4-methylenedioxyphenyl.

Condensation with 3,4-methylenedioxyaniline (1.23 g) according to the general procedure at room temperature for 66 h followed by filtration affords 2.66 g (71%) of the title compound as a greenish solid. Physical characteristics: M.p. 117–118° C.; $^1$H NMR (300 MHz, DMSO-$d_6$) o 12.29, 10.80, 8.40, 8.29, 7.45–7.11, 6.97–6.89, 6.08, 6.06, 3.98–3.90, 3.57, 3.48, 2.35, 0.94, 0.81; IR (diffuse reflectance) 1691, 1662, 1613 (s), 1572 (s), 1508, 1466, 1432, 1319, 1278, 1270, 1258 (s), 1244, 1231, 1206 (s), 1111 (s) cm$^{-1}$; MS (ESI+) m/z 457 (100, (M+H)$^+$), 458 (23). Anal. Calcd for $C_{24}H_{25}FN_2O_6$: C, 63.15; H, 5.52; N, 6.14; F, 4.16. Found: C, 63.15; H, 5.57; N, 6.15; F, 4.08.

PREPARATION 5j

Ethyl 2-(2-Fluoro-5-(4-morpholinylmethyl)benzoyl)-3-(1H-indol-5-ylamino)-2-propenoate [A.3, W=morpholinylmethyl, aryl=5-indole Condensation with 5-aminoindole (1.19 g) according to the general procedure at room temperature for 90 h followed by purification by column chromatography (CH$_2$Cl$_2$/methanol, 100/1; 50/1; 33/1) affords 3.09 g (84%) of the title compound as a yellow amorphous solid. Physical characteristics: $^1$H NMR (400 MHz, DMSO-$d_6$) δ 12.60, 11.27, 11.24, 11.00, 8.54, 8.44, 7.68, 7.61, 7.48–7.12, 6.49, 6.46, 3.99–3.92, 3.58, 3.48, 2.36, 0.95, 0.83; IR (diffuse reflectance) 1671, 1628 (s), 1613 (s), 1564, 1429 (s), 1407, 1307 (s), 1285 (s), 1254 (s), 1221, 1212 (b), 1116, 1103, 864, 761 cm$^1$; MS (ESI+) m/z 452 (100, (M+H)+), 453 (22); HRMS calcd for $C_{25}H_{26}FN_3O_4$+H m/z 452.1985, found 452.1983.

PREPARATION 5k

Ethyl 2-(2-Fluoro-5-(4-morpholinylmethyl)benzoyl)-3-(3-hydroxyanilino)-2-propenoate [A.3, W=morpholinylmethyl, aryl=3-hydroxyphenyl Condensation with 3-aminophenol (0.98 g) according to the general procedure at room temperature for 18 h followed by purification by column chromatography (CH$_2$Cl$_2$/methanol, 100/1; 50/1; 33/1) affords 2.89 g (82%) of the title compound as a light yellow amorphous solid. Physical characteristics: $^1$H NMR (300 MHz, DMSO-$d_6$) δ 12.14, 10.71, 9.80, 8.45, 8.31, 7.44–7.11, 6.93–6.60, 4.00–3.91, 3.57, 3.46, 2.35, 0.94, 0.83; IR (diffuse reflectance) 1694, 1671, 1629 (s), 1604 (s), 1569 (s), 1493, 1430, 1302 (s), 1281 (s), 1256 (s), 1209, 1180, 1155, 1115, 1106 cm-; MS (ESI+) m/z 429 (100, (M+H)$^+$), 430 (22); HRMS calcd for $C_{23}H_{25}FN_2O_5$+H m/z 429.1826, found 429.1846.

PREPARATION 5l

Ethyl 2-(2-Fluoro-5-(4-morpholinylmethyl)benzoyl)-3-(3-(2-hydroxyethyl)anilino)-2-propenoate [A.3, W=morpholinylmethyl, aryl=3-(2-hydroxyethyl)-phenyl 3-Nitrophenethyl alcohol (1.50 g) is added to a suspension of Pd/C (10%, 500 mg) in ethanol (15 mL). The mixture is placed under hydrogen gas pressure (35 psi) in a Parr hydrogenator for 1 h. The catalyst is removed by filtration through Celite and the solution is concentrated to afford 3-aminophenethyl alcohol. Condensation with the resulting crude aniline according to the general procedure at room temperature for 36 followed by purification by column chromatography (CH$_2$Cl$_2$/methanol, 100/1; 50/1; 33/1; 20/1) affords 2.94 g (78%) of the title compound as an orange amorphous solid. Physical characteristics: $^1$H NMR (400 MHz, DMSO-$d_6$) δ 12.26, 10.82, 8.53, 8.41, 7.46–7.26, 7.19–7.06, 4.68, 3.99–3.92, 3.67–3.61, 3.58, 3.48, 2.77, 2.36, 0.93, 0.82; IR (liq.) 1696, 1672, 1627 (s), 1610 (s), 1591 (s), 1571 (s), 1494, 1428 (s), 1301 (s), 1281 (s), 1259 (s), 1233, 1208, 1117 (s), 1104 cm-; MS (ESI+) m/z 457 (100, (M+H)+), 458 (25). HRMS calcd for $C_{25}H_{29}FN_2O_5$+H m/z 457.2138, found 457.2143.

PREPARATION 5m

Ethyl-2-[2-fluoro-5-(4-morpholinylmethyl)benzoyl]-3-(3-methoxyanilino)-2-propenoate [A.3, W=morpholinylmethyl, aryl=3-methoxyphenyl.

Condensation of 3-methoxyaniline (1.0 mL) according to the general procedure at room temperature for 18 h followed by purification by column chromatography (CH$_2$C$_{12}$/methanol, 99/1, 98/2) affords 1.26 g (36%) of the title compound as an orange oil. Physical characteristics: $^1$H NMR (300 MHz, DMSO-$d_6$) δ 12.18, 10.78, 8.51, 8.39, 7.47–7.28, 7.21–6.98, 6.85–6.74, 3.95, 3.80, 3.57, 3.48, 2.35, 0.94, 0.82; IR (liq.) 1700 (s), 1629 (s), 1606 (s), 1598 (s), 1571 (s), 1495, 1427 (s), 1293 (s), 1282 (s), 1266 (s), 1252 (s), 1242 (s), 1209, 1155, 1117 (s) cm-; MS (ESI) n/z 443 (M+H)$^+$. Anal. Calcd for $C_{24}H_{27}FN_2O_5$: C, 65.15; H, 6.15; N, 6.33; F, 4.29. Found: C, 64.79; H, 5.84; N, 6.39; F, 4.09.

PREPARATION 5n

Ethyl-2-[2-fluoro-5-(4-morpholinylmethyl)benzoyl]-3-[3-(hydroxymethyl)anilino]-2-propenoate [A.3, W=morpholinylmethyl, aryl=3-(hydroxymethyl)phenyl.

Condensation of 3-(hydroxymethyl)aniline (1.1 g) according to the general procedure at 50° C. for 4 h followed by purification by column chromatography (CH$_2$Cl$_2$/methanol, 99/1, 98/2, 96/4; followed by EtOAc/heptane, 2/1, 4/1, 8/1, 20/1) affords 1.28 g (36%) of the title compound as a yellow oil which solidifies upon standing. Physical characteristics: $^1$H NMR (300 MHz, DMSO-$d_6$) δ 12.27, 10.83, 8.52, 8.41, 7.46–7.29, 7.23–7.11, 5.31, 4.53, 3.95, 3.57, 3.48, 2.35, 1.06, 0.93, 0.82; IR (diffuse reflectance) 1675 (s), 1627, 1609 (s), 1594 (s), 1564 (s), 1459, 1428, 1311, 1294 (s), 1279 (s), 1262 (s), 1233, 1208, 1178, 1111 (s) cm$^{-1}$; MS (ESI) n/z 443 (M+H)+; Anal. Calcd for $C_{24}H_{27}FN_2O_5$: C, 65.15; H, 6.15; N, 6.33. Found: C, 65.03; H, 6.21; N, 6.28.

PREPARATION 5o

Ethyl 2-[2-fluoro-5-(4-morpholinylmethyl)benzoyl]-3-[4-(4-morpholinyl)anilino]-2-propenoate [A.3, W=morpholinylmethyl, aryl=4-(4-morpholinyl)phenyl.

Condensation of 4-morpholinoaniline (1.6 g) according to the general procedure at room temperature for 18 h affords 3.97 g (98%) of the title compound as a brown solid. Physical characteristics: $^1$H NMR (400 MHz, DMSO-$d_6$) δ 12.38, 10.85, 8.44, 8.40, 7.43–7.33, 7.31–7.27, 7.18–7.10, 7.04–6.98, 3.97–3.89, 3.75, 3.57, 3.48, 3.13, 2.35, 0.93, 0.81; MS (ESI+) m/z 498 (M+H)$^+$.

PREPARATION 5p

Ethyl 3-(3,4-difluoroanilino)-2-[2-fluoro-5-(4-morpholinylmethyl)benzoyl]-2-propenoate [A.3, W=morpholinylmethyl, aryl=3,4-difluorophenyl.

Condensation of 3,4-difluoroaniline (0.88 mL) according to the general procedure at 50° C. for 18 h followed by purification by recrystallization from ethanol affords 2.23 g (61%) of the title compound as a beige solid. Physical characteristics: M.p. 125–128° C.; $^1$H NMR (300 MHz, DMSO-$d_6$) δ 12.1, 10.21, 8.51–8.24, 7.87–7.68, 7.56–7.28, 7.15, 3.95, 3.57, 3.48, 2.35, 0.99–0.77; IR (diffuse reflectance) 1694, 1665, 1637, 1632, 1613 (s), 1574 (s), 1523 (s), 1430, 1295 (s), 1276, 1256 (s), 1231, 1217, 1209 (s), 1109 (s) cm-]; MS (ESI) m/z 449 (M+H)+; Anal. Calcd for $C_{23}H_{23}F_3N_2O_4$: C, 61.60; H, 5.17; N, 6.25; F, 12.71. Found: C, 61.54; H, 5.27; N, 6.21; F, 13.10.

General Preparation A.4. Method A. Sodium hydride (60% dispersion, 1.2 equiv) is added to a solution of the corresponding intermediate A.3 (General Preparation A.3) in THF (0.5 M). The mixture is heated to 70° C. for 3 h. The reaction mixture is quenched with water (5 mL) and concentrated in vacuo. The crude product is purified by either filtration or column chromatography to afford the desired intermediate A.4. Method B. Potassium t-butoxide (1.1 equiv) is added to a solution of the corresponding intermediate A.3 (General Preparation A.3) in t-butanol and the mixture is stirred at 60° C. for 18–20 h. The reaction mixture is concentrated in vacuo to a slurry which is filtered and washed with water and diethyl ether. The crude product is purified by either recrystallization or column chromatography to afford the desired intermediate A.4. Method C. A mixture of potassium carbonate (1.5 equiv) and the corresponding intermediate A.3 (General Preparation A.3) in DMF (0.2 M) is heated at 85° C. for 0.5–8 h. The mixture is allowed to cool to room temperature and is poured into water. The crude product is purified as described below to afford the desired intermediate A.4.

The following compounds (Preparations 6a–6p) are prepared according to one of these procedures.

PREPARATION 6a

Ethyl 6-(4-Morpholinylmethyl)4-oxo-1-phenyl-1,4-dihydro-3-quinolinecarboxylate [A.4, W=morpholinylmethyl, aryl=phenyl]

According to general method A, ethyl 3-anilino-2-(2-fluoro-5-(4-morpholinylmethyl)-benzoyl)-2-propenoate (Preparation 5a, 1.0 g) affords upon filtration and drying 0.46 g (48%) of the title compound as an orange solid. Physical characteristics: M.p. 159–161° C.; $^1$HNMR (300 MHz, DMSO-$d_6$) δ 8.43, 8.20, 7.67, 7.60, 6.94, 4.21, 3.58–3.55, 2.36–2.32, 1.25; IR (drift) 1683, 1644, 1609, 1490, 1348, 1320, 1257, 1244, 1166, 1111, 865, 803 cm-; MS (ESI+) m/z 393 (M+H)+; Anal. Calcd for $C_{23}H_{24}N_2O_4$: C, 70.39; H, 6.16; N, 7.14. Found: C, 70.28; H, 6.33; N, 6.97.

PREPARATION 6b

Ethyl 1-(2-Methylphenyl)-6-(4-morpholinylmethyl)-4-oxo-1,4-dihydro-3-quinoline-carboxylate [A.4, W=morpholinylmethyl, aryl=2-methylphenyl]

According to general method A, ethyl 2-(2-fluoro-5-(4-morpholinylmethyl)benzoyl)-3-(2-toluidino)-2-propenoate (Preparation 5b, 1.0 g) affords after purification by column chromatography ($CH_2Cl_2$/MeOH, 99/1, 97/3, 96/4) to afford 1.05 g (91%) of the title compound as a yellow oil. Physical characteristics: $^1$H NMR (300 MHz, DMSO-$d_6$) δ 8.40, 8.21, 7.62–7.45, 6.73, 4.20, 3.58, 2.36, 2.01, 1.26; MS (ESI+) m/z 407 (M+H)+; HRMS (FAB) calcd for $C_{24}H_{26}N_2O_4$+H m/z 407.1971, found 407.1969.

PREPARATION 6c

Ethyl 1-(3-iodophenyl)-6-(4-morpholinylmethyl)-4-oxo-1,4-dihydro-3-quinoline-carboxylate [A.4, W=morpholinylmethyl, aryl=3-iodophenyl.

According to general method B, ethyl 2-[2-fluoro-5-(4-morpholinylmethyl)benzoyl]-3-(3-iodoanilino)-2-propenoate (Preparation 5c, 3.65 g) affords after recrystallization from acetonitrile 1.417 g (40%) of the title compound as a light yellow powder. Physical characteristics: M.p. 209–212° C.; $^1$H NMR (300 MHz, DMSO-$d_6$) δ 8.44, 8.14, 8.02, 7.70, 7.6, 7.44, 6.94, 4.21, 3.65–3.53, 2.41–2.31, 1.26; 13C NMR (75 MHz, CDCl$_3$) δ 192.2, 189.3, 168.9, 151.9, 151.3, 140.5, 135.2, 132.9, 131.7, 130.7, 127.1, 126.6, 117.7, 117.0, 115.5, 115.3, 106.0, 95.4, 67.3, 62.8, 60.7, 60.423, 53.9, 14.3, 13.9; IR (drift) 1693, 1663, 1615, 1583, 1560, 1295, 1278, 1271, 1261, 1255, 1241, 1232, 1214, 1110, 769 cm$^{-1}$; MS (ESI+) m/z 539 (M+H)+; Anal. Calcd for $C_{23}H_2O_4FIN_2O_4$: C, 51.31; H, 4.49; N, 5.20; Found: C, 51.30; H, 4.52; N, 5.14.

PREPARATION 6d

Ethyl 1-(4-chlorophenyl)-6-(4-morpholinylmethyl)-4-oxo-1,4-dihydro-3-quinoline-carboxylate [A.4, W=morpholinylmethyl, aryl=4-chlorophenyl.

According to general method B, ethyl 3-(4-chloroanilino)-2-(2-fluoro-5-(4-morpholinylmethyl)benzoyl)-2-propenoate (Preparation 5d, 2.5 g) affords after recrystallization from ethanol 1.51 g (63%) of the title compound as an off-white crystalline powder. Physical characteristics: M.p. 178–181° C. $^1$H NMR (300 MHz, DMSO-$d_6$) δ 8.45, 8.19, 7.77–7.69, 7.60, 6.96, 4.21, 3.61–3.52, 2.39–2.32, 1.26; $^3$C NMR (75 MHz, CDCl$_3$) δ 174.7, 165.9, 148.6, 140.0, 139.5, 136.6, 136.1, 133.8, 131.1, 129.2, 128.5, 128.1, 117.9, 112.1, 67.4, 62.9, 61.4, 53.9, 14.8; IR (diffuse reflectance) 1718, 1608, 1489, 1365, 1347, 1333, 1324, 1255, 1246, 1212, 1165, 1117, 1087, 844, 822 cm$^{-1}$. HRMS (FAB) calcd for $C_{23}H_{23}ClN_2O_4$+H m/z 427.1424, found 427.1419. Anal. Calcd for $C_{23}H_{23}ClN_2O_4$: C, 64.71; H, 5.43; N, 6.56; Cl, 8.31. Found: C, 64.35; H, 5.47; N, 6.47; Cl, 8.23.

PREPARATION 6e

Ethyl 1-(4-isopropylphenyl)-6-(4-morpholinylmethyl)-4-oxo-1,4-dihydro-3-quinoline-carboxylate [A.4, W=morpholinylmethyl, aryl=4-isopropylphenyl.

According to general method B, ethyl-2-(2-fluoro-5-(4-morpholinylmethyl)benzoyl)-3(4-isopropylanilino)-2-propenoate (Preparation 5e, 3.00 g) affords after recrystallization from isopropanol 1.294 g (45%) of the title compound as a yellow powder. Physical characteristics: M.p. 181–184° C.; $^1$H NMR (300 MHz, DMSO-$d_6$) δ 8.42, 8.19, 7.61, 7.57–7.51, 6.95, 4.21, 3.57, 3.05, 2.36, 1.31–1.22; 13C NMR (75 MHz, CDCl$_3$) δ 174.8, 166.1, 151.5, 149.0, 140.3, 138.7, 135.7, 133.6, 128.7, 128.5, 127.9, 127.5, 118.4, 111.7, 67.4, 62.9, 61.3, 53.9, 34.4, 25.8, 24.3, 14.8; IR (drift) 1726, 1605, 1510, 1486, 1384, 1359, 1334, 1317, 1244, 1217, 1164, 1114, 1084, 862, 828 cm$^{-1}$; HRMS (FAB) calcd for $C_{26}H_{30}N_2O_4$+H m/z 435.2284, found 435.2278.

PREPARATION 6f

Ethyl 1-(4-methoxyphenyl)-6-(4-morpholinylmethyl)-4-oxo-1,4-dihydro-3-quinoline-carboxylate [A.4, W=morpholinylmethyl, aryl=4-mothoxyphenyl.

According to general method B, ethyl 2-[2-fluoro-5-(4-morpholinylmethyl)benzoyl]-3-(4-methoxyanilino)-2-propenoate (Preparation 5f, 2.00 g) affords after recrystallization from isopropanol 0.946 g (50%) of the title compound as a yellow powder. Physical characteristics: M.p. 177–179° C.; $^1$H NMR (300 MHz, DMSO-d$_6$) δ 8.4, 8.18, 7.61, 7.59–7.56, 7.22–7.16, 6.95,4.20, 3.87, 3.57, 2.38–2.33, 1.26; $^{13}$C NMR (75 MHz, CDCl$_3$) δ 172.7, 164.1, 158.8, 147.2, 138.5, 133.6, 131.7, 131.6, 126.8, 126.4, 125.8, 116.3, 113.7, 109.6, 65.3, 60.9, 59.2, 54.1, 51.8, 12.8; IR (drift) 1721, 1608, 1512, 1486, 1365, 1346, 1330, 1300, 1248, 1172, 1163, 1115, 1086, 1029, 808 cm-; HRMS (FAB) calcd for $C_{24}H_{26}N_2O_5$+H m/z 423.1920, found 423.1925.

PREPARATION 6g

Ethyl 1-(2-(Hydroxymethyl)phenyl)-6-(4-morpholinylmethyl)-4-oxo-1,4-dihydro-3-quinolinecarboxylate [A.4, W=morpholinylmethyl, aryl=2-hydroxymethylphenyl.

Ethyl 2-(2-fluoro-5-(4-morpholinylmethyl)benzoyl)-3-(2-(hydroxymethyl)anilino)-2-propenoate (Procedure 5g, 2.79 g) is reacted according to general method C for 1 h.

The resulting mixture is extracted with EtOAc (3×50 mL). The combined organic layers are washed with brine (5 mL), dried (Na$_2$SO$_4$), and concentrated. The crude product is crystallized from ethanol to afford 1.54 g (58%) of the title compound as a light yellow solid. Physical characteristics: M.p. 164–166° C.; $^1$H NMR (400 MHz, DMSO-d$_6$) δ 8.41, 8.20, 7.74, 7.68, 7.60–7.56, 6.71, 5.26, 4.25–4.15, 3.58, 2.37, 1.26; $^3$C NMR (100 MHz, DMSO-d$_6$) δ 173.4, 164.5, 148.9, 139.7, 139.6, 138.3, 135.4, 134.0, 130.7, 129.7, 129.4, 128.6, 127.5, 126.4, 118.1, 110.8, 66.5, 62.0, 60.2, 59.2, 56.4, 53.5, 14.6; IR (diffuse reflectance) 1691 (s), 1634, 1609 (s), 1601 (s), 1549, 1489 (s), 1322, 1276, 1244 (s), 1224, 1181, 1142, 1113, 806, 783 cm$^{-1}$; MS (ESI+) n/z 423 (100, (M+H)+), 424 (23); HRMS calcd for $C_{24}H_{26}N_2O_5$+H m/z 423.1920, found 423.1902. Anal. Calcd for $C_{24}H_{26}N_2O_5$: C, 68.23; H, 6.20; N, 6.63. Found: C, 68.24; H, 6.31; N, 6.58.

PREPARATION 6h

Ethyl 1-(2,3-Dihydro-1 H-inden-5-yl)-6-(4-morpholinylmethyl)-4-oxo-1,4-dihydro-3-quinolinecarboxylate [A.4, W=morpholinylmethyl, aryl=indan Ethyl 3-(2,3-dihydro-1H-inden-5-ylamino)-2-(2-fluoro-5-(4-morpholinylmethyl)-benzoyl)-2-propenoate (Procedure 5h, 2.0 g) is reacted according to general method C for 8 h. The resulting mixture is extracted with EtOAc (3×50 mL). The combined organic layers are washed with brine (5 mL), dried (Na$_2$SO$_4$), and concentrated. The crude product is triturated with diethyl ether and recrystallized from EtOAc/hexane to afford 1.55 g (81%) of the title compound as a light yellow solid. Physical characteristics: M.p. 133–135° C.; $^1$H NMR (400 MHz, DMSO-d$_6$) δ 8.41, 8.19, 7.60, 7.50, 7.49, 7.37, 6.98, 4.21, 3.58, 2.98, 2.36, 2.13, 1.26; $^{13}$C NMR (100 MHz, DMSO-d$_6$) δ 173.3, 164.5, 148.7, 146.6, 146.1, 140.1, 139.0, 135.5, 133.8, 127.6, 126.4, 126.0, 125.6, 123.7, 118.6, 110.6, 66.5, 62.0, 60.2, 53.4, 32.7, 32.5, 25.6, 14.6; IR (diffuse reflectance) 2953, 2813, 1686 (s), 1641 (s), 1608 (s), 1550, 1489 (s), 1321, 1264, 1249 (s), 1220, 1174, 1115, 862, 802 cm-; MS (ESI+) m/z 433 (100, (M+H)+), 434 (28). Anal. Calcd for $C_{26}H_{28}N_2O_4$: C, 72.20; H, 6.53; N, 6.48. Found: C, 72.30; H, 6.57; N, 6.46.

PREPARATION 6i

Ethyl 1-(1,3-Benzodioxol-5-yl)-6-(4-morpholinylmethyl)-4-oxo-1,4-dihydro-3-quinolinecarboxylate [A.4, W=morpholinylmethyl, aryl=3,4-methylenedioxyphenyl.

Ethyl 3-(1,3-benzodioxol-5-ylamino)-2-(2-fluoro-5-(4-morpholinylmethyl)benzoyl)-2-propenoate (Procedure 5i, 2.53 g) is reacted according to general method C for 8 h.

The resulting precipitate is filtered and recrystallized from ethanol to afford 1.55 g (64%) of the title compound as a gray solid. Physical characteristics: M.p. 173–174 ° C.; $^1$H NMR (400 MHz, DMSO-d$_6$) δ 8.41, 8.18, 7.61, 7.33, 7.16, 7.13, 7.03, 6.20, 4.21, 3.58, 2.36, 1.26; $^{13}$C NMR (100 MHz, DMSO-d$_6$) o 173.4, 164.5, 148.9, 148.7, 148.6, 140.3, 135.3, 134.5, 133.8, 127.6, 126.3, 121.7, 118.6, 110.6, 109.3, 109.0, 102.7, 66.5, 62.0, 60.2, 56.4, 53.4, 18.9, 14.6; IR (diffuse reflectance) 3046 (w), 2804, 1691, 1644, 1608, 1489 (s), 1452 (w), 1349 (w), 1321, 1277 (w), 1250, 1225 (s), 1117, 1031, 866 (w) cm-; MS (ESI+) m/z 437 (100, (M+H)+), 438 (23); HRMS calcd for $C_{24}H_{24}N_2O_6$+H m/z 437.1712, found 437.1714. Anal. Calcd for $C_{24}H_{24}N_2O_6$: C, 66.04; H, 5.54; N, 6.42. Found: C, 65.80; H, 5.67; N, 6.33.

PREPARATION 6j

Ethyl 1-(1H-Indol-5-yl)-6-(4-morpholinylmethyl)-4-oxo-1,4-dihydro-3-quinoline-carboxylate [A.4, W=morpholinylmethyl, aryl=5-indole Ethyl 2-(2-fluoro-5-(4-morpholinylmethyl)benzoyl)-3-(1H-indol-5-ylamino)-2-propenoate (Procedure 5j, 2.94 g) is reacted according to general method C for 2 h. The resulting mixture is extracted with EtOAc (3×50 mL). The combined organic layers are washed with brine (5 mL), dried (Na$_2$SO$_4$), and concentrated. The crude product is purified by column chromatography (CH$_2$Cl$_2$/methanol, 50/1; 33/1; 25/1; 13/1) to afford 1.98 g (71%) of the title compound as a white solid. Physical characteristics: M.p. 207–210° C.; $^1$H NMR (400 MHz, DMSO-d$_6$) δ 11.55, 8.49, 8.20, 7.82, 7.63, 7.58, 7.56, 7.26, 6.97, 6.58, 4.21, 3.57, 2.36, 1.25; $^{13}$C NMR (100 MHz, DMSO-d$_6$) δ 173.4, 164.6, 149.3, 140.7, 136.1, 135.2, 133.7, 132.8, 128.4, 127.6, 126.3, 120.2, 119.3, 119.0, 113.1, 110.3, 102.3, 66.5, 62.1, 60.1, 56.4, 53.4, 14.6; IR (diffuse reflectance) 3313, 1721 (s), 1683, 1628, 1605 (s), 1485 (s), 1349, 1319, 1291, 1250, 1234, 1181, 1119, 821, 732 cm-; MS (ESI+) m/z 432 (100, (M+H)+), 433 (26). Anal. Calcd for $C_{25}H_{25}N_3O_4$: C, 69.59; H, 5.84; N, 9.74. Found: C, 69.36; H, 5.95; N, 9.61.

PREPARATION 6k

Ethyl 1-(3-Hydroxyphenyl)-6-(4-morpholinylmethyl)-4-oxo-1,4-dihydro-3-quinoline-carboxylate [A.4, W=morpholinylmethyl, aryl=3-hydroxyphenyl.

Ethyl-2-(2-fluoro-5-(4-morpholinylmethyl)benzoyl)-3-(3-hydroxyanilino)-2-propenoate (Procedure 5k, 2.78 g, 6.5 mmol) is reacted according to general method C for 2 h. The resulting mixture is extracted with EtOAc (3×50 mL). The combined organic layers are washed with brine (5 mL), dried (Na$_2$SO$_4$), and concentrated. The aqueous layer is neutralized with saturated aqueous ammonium chloride and the resulting precipitate is filtered and combined with the preceding concentrate. The crude product is purified by column chromatography (CH$_2$Cl$_2$/methanol, 50/1; 33/1; 20/1; 13/1) to afford 1.33 g (50%) of the title compound as a white solid. Physical characteristics: M.p. 245–246° C.; $^1$H NMR (400 MHz, DMSO-d$_6$) δ 10.14, 8.41, 8.18, 7.62, 7.46, 7.05–7.02, 6.97, 4.21, 3.57, 2.36, 1.26; IR (diffuse reflectance) 1719 (s), 1608 (s), 1549, 1488 (s), 1467, 1449, 1366, 1350, 1327, 1226 (s), 1173, 1116, 1089, 866, 811 cm$^1$; MS (ESI+) m/z 409 (100, (M+H)+), 410 (24), 431 (66, (M+Na)$^+$). Anal. Calcd for C$_{23}$H$_{24}$N$_2$O$_5$: C, 67.63; H, 5.92; N, 6.86. Found: C, 67.54; H, 5.98; N, 6.84.

PREPARATION 6l

Ethyl 1-(3-(2-Hydroxyethyl)phenyl)-6-(4-morpholinyl-methyl)-4-oxo-1,4-dihydro-3-quinolinecarboxylate [A.4, W=morpholinylmethyl, aryl =3-(2-hydroxyethyl)-phenyl.

Ethyl 2-(2-fluoro-5-(4-morpholinylmethyl)benzoyl)-3-(3-(2-hydroxyethyl)anilino)-2-propenoate (Procedure 5l, 2.73 g) is reacted according to general method C for 2 h.

The resulting mixture is extracted with EtOAc (3×50 mL). The combined organic layers are washed with brine (5 mL), dried (Na$_2$SO$_4$), and concentrated. The crude product is purified by recrystallization from EtOAc/hexane to afford 1.85 g (71%) of the title compound as a light yellow solid. Physical characteristics: -M.p. 161–162° C.; $^1$H NMR (400 MHz, DMSO-d$_6$) δ 8.43, 8.20, 7.61, 7.57 (d, J =7.5 Hz, 1 H), 7.52–7.46, 6.98, 4.70, 4.22, 3.68, 3.58, 2.84, 2.37, 1.26; $^{13}$C NMR (100 MHz, DMSO-d$_6$) δ 173.3, 164.6, 148.5, 142.8, 140.6, 139.9, 135.4, 133.9, 130.8, 130.3, 128.2, 127.6, 126.4, 125.3, 118.5, 110.7, 66.5, 62.0, 61.9, 60.2, 53.4, 14.6; IR (diffuse reflectance) 3418, 2951, 2932, 1680 (s), 1634, 1607 (s), 1548, 1487 (s), 1360, 1322 (s), 1275, 1251 (s), 1133, 1114, 808 cm$^{-1}$; MS (ESI+) n/z 437 (100, (M+H)+), 438 (15). Anal. Calcd for C$_{25}$H$_{28}$N$_2$O$_5$: C, 68.79; H, 6.47; N, 6.42. Found: C, 68.68; H, 6.51; N, 6.36.

PREPARATION 6m

Ethyl 1-(3-methoxyphenyl)-6-(4-morpholinylmethyl)-4-oxo-1,4-dihydro-3-quinoline-carboxylate [A.4, W=morpholinylmethyl, aryl =3-methoxyphenyl According to general method C, ethyl 2-(2-fluoro-5-(4-morpholinylmethyl)benzoyl)-3-(3-methoxyanilino)-2-propenoate (Preparation 5m, 0.44 g) affords after recrystallization from ethanol 295 mg (70%) of the title compound as a light yellow solid. Physical characteristics: M.p. 199–202° C.; $^1$H NMR (400 MHz, DMSO-d$_6$) δ 8.43, 8.19, 7.63–7.55, 7.30, 7.21, 7.00, 4.21, 3.8, 3.60–3.55, 2.38–2.36, 1.27; IR (diffuse reflectance) 1724 (s), 1602 (s), 1489, 1403, 1361, 1317, 1269, 1229, 1219, 1161, 1156, 1132, 1113, 1085, 1033 cm-; MS (ESI) m/z 423 (M+H)+. Anal. Calcd for C$_{24}$H$_{26}$N$_2$O$_5$: C, 68.23; H, 6.20; N, 6.63. Found: C, 68.29; H, 6.25; N, 6.54.

PREPARATION 6n

Ethyl 1-[3-(hydroxymethyl)phenyl]-6-(4-morpholinyl-methyl)-4-oxo-1,4-dihydro-3-quinolinecarboxylate [A.4, W=morpholinylmethyl, aryl =3-(hydroxymethyl)phenyl According to general method C, ethyl-2-(2-fluoro-5-(4-morpholinylmethyl)benzoyl)-3-(2-(hydroxymethyl)anilino)-2-propenoate (Preparation 5n, 1.2 g) affords after recrystallization from ethanol 257 mg (23%) of the title compound as a light yellow solid. Physical characteristics: M.p. 193–196° C.; $^1$H NMR (300 MHz, DMSO-d$_6$) δ 8.42, 8.20, 7.66–7.50, 6.95, 5.41, 4.62, 4.21, 3.60–3.53, 2.36, –1.26; IR (diffuse reflectance) 3389, 1715 (s), 1605 (s), 1552, 1487 (s), 1360, 1348, 1320, 1247, 1217, 1167, 1118, 1087, 864, 808 cm-; MS (ESI) m/z 423 (M+H)+. Anal. Calcd for C$_{24}$H$_{26}$N$_2$O$_5$: C, 68.23; H, 6.20; N, 6.63. Found: C, 68.08; H, 6.18; N, 6.59.

PREPARATION 6o

Ethyl 6-(4-morpholinylmethyl)-1-[4-(4-morpholinyl)phenyl]-4-oxo-1,4-dihydro-3-quinolinecarboxylate [A.4, W=morpholinylmethyl, aryl =4-morpholinylphenyl According to general method C, ethyl 2-(2-fluoro-5-(4-morpholinylmethyl)benzoyl)-3-(4-(4-morpholinyl)anilino)-2-propenoate (Procedure 5o, 1.8 g) affords 1.27 g (75%) of the title compound. Physical characteristics: M.p. 214–217° C.; $^1$H NMR (400 MHz, DMSO-d$_6$) δ 8.38, 8.18, 7.60, 7.46, 7.15, 7.00, 4.21, 3.78, 3.58, 3.25, 2.36, 1.26; IR (diffuse reflectance) 1732 (s), 1630, 1609 (s), 1516 (s), 1485, 1361, 1332, 1320, 1261, 1246 (s), 1217, 1119 (s), 1086, 925, 833 cm-; HRMS (FAB) calcd for C$_{27}$H$_{31}$N$_3$O$_5$+H m/z 478.2342, found 478.2358.

PREPARATION 6p

Ethyl 1-(3,4-difluorophenyl)-6-(4-morpholinylmethyl)-4-oxo-1,4-dihydro-3-quinoline-carboxylate [A.4, W=morpholinylmethyl, aryl =3,4-difluorophenyl.

According to general method C, ethyl 3-(3,4-difluoroanilino)-2-(2-fluoro-5-(4-morpholinylmethyl)benzoyl)-2-propenoate (Preparation 5p, 1.0 g) affords after recrystallization from ethanol 520 mg (37%) of the title compound as a yellow solid. Physical characteristics: M.p. 214–217° C.; $^1$H NMR (400 MHz, DMSO-d$_6$) δ 8.48, 8.18, 8.03–7.97, 8.00, 7.63–7.58, 7.01, 4.21, 3.60–3.54, 2.36, 1.27; IR (diffuse reflectance) 1695, 1639, 1608, 1517 (s), 1488, 1289, 1267, 1232, 1178, 1118, 1113, 865, 826, 803, 779 cm-; MS (ESI) m/z 429 (M+H)+. Anal. Calcd for C$_{23}$H$_{22}$F$_2$N$_2$O$_4$: C, 64.48; H, 5.18; N, 6.54; F, 8.87. Found: C, 64.36; H, 5.22; N, 6.50; F, 8.99.

General Preparation A.5. A mixture of quinoline ester obtained according to General Preparation A.4 and a substituted benzylamine (5 equiv) is heated to 180° C. for a period of 1–24 h. The reaction mixture is allowed to cool to rt. The crude product may be either purified by column chromatography or precipitated by trituration with an appropriate solvent followed by recrystallization. The following compounds (Examples 1–18) are prepared according to these procedures.

EXAMPLE 1

N-(4-Chlorobenzyl)-6-(4-morpholinylmethyl)-4-oxo-1-phenyl-1,4-dihydro-3-quinolinecarboxamide [A.5, W=morpholinylmethyl, aryl =phenyl, X=Cl]

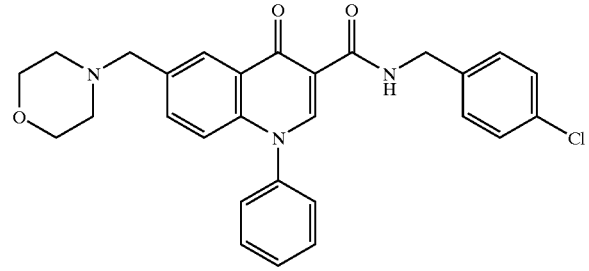

The title compound is prepared according to general preparation A.5 employing the product of Preparation 6a (0.42 g) and 4-chlorobenzylamine (0.63 mL). The crude product is triturated with diethyl ether, filtered, and recrystallized (2-propanol) to afford the title compound as an off-white solid (49%). Physical characteristics: M.p. 168–169° C.; $^1$H NMR (300 MHz, DMSO-d$_6$) δ 10.36, 8.59, 8.29, 7.68–7.66, 7.40, 7.05, 4.56, 3.58, 3.58–3.55, 2.38–2.35; ¹³C NMR (75 MHz, DMSO-d₆) δ 175.8, 164.0, 147.4, 140.5, 139.6, 138.6, 135.4, 134.0, 131.4, 130.4, 130.1, 129.2, 128.3, 127.4, 126.3, 125.7, 118.3, 110.9, 66.2, 61.6, 53.1, 41.5; IR (drift) 1660, 1603, 1585, 1540, 1488, 1335, 1323, 1314, 1237, 1110, 1003, 809 cm¹; MS (ESI+) m/z 488 (M+H)⁺. Anal. Calcd for $C_{28}H_{26}ClN_3O_3$: C, 68.92; H, 5.37; N, 8.61; Cl, 7.26. Found: C, 68.65; H, 5.38; N, 8.57; Cl, 7.53.

EXAMPLE 2

N-(4-Chlorobenzyl)-1-(2-methylphenyl)-6-(4-morpholinylmethyl)-4-oxo-1,4-dihydro-3-quinolinecarboxamide [A.5, W=morpholinylmethyl, aryl=2-methylphenyl, X=

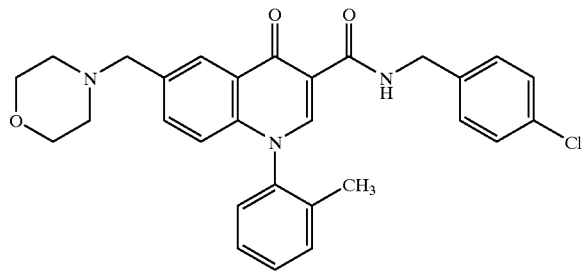

The title compound is prepared according to general preparation A.5 employing the product of Preparation 6b (0.41 g) and 4-chlorobenzylamine (0.62 mL). The crude product is purified by column chromatography (CH₂Cl₂/MeOH, 99/1, 98/2) and recrystallization (diethyl ether) to afford the title compound as a beige solid (26%). Physical characteristics: M.p. 148–150° C.; ¹H NMR (300 MHz, DMSO-d₆) δ 10.37, 8.55, 8.31, 7.67, 7.62–7.48, 7.43–7.36, 6.84, 4.57, 3.61, 3.57, 2.37, 1.98; IR (drift) 1665, 1601, 1574, 1549, 1487, 1328, 1318, 1242, 1108,827,810,794, 779cm-[;MS (ESI+) in/z 502 (M+H)⁺. Anal. Calcd for $C_{29}H_{28}ClN_3O_3$: C, 69.38; H, 5.62; N, 8.37; Cl, 7.06. Found: C, 69.04; H, 5.70; N, 8.27; Cl, 7.12.

EXAMPLE 3

N-(4-Chlorobenzyl)-1-(3-iodophenyl)-6-(4-morpholinylmethyl)-4-oxo-1,4-dihydro-3-quinolinecarboxamide [A.5 W=morpholinylmethyl, aryl=3-iodophenyl, X=Cl

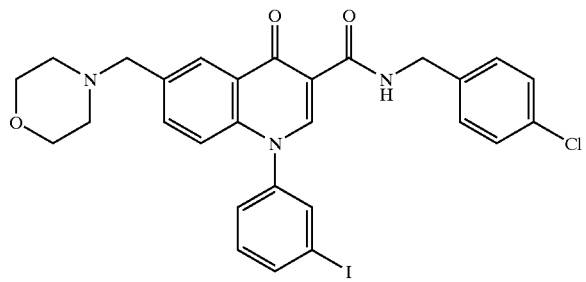

The title compound is prepared according to general preparation A.5 employing the product of Preparation 6c (0.50 g) and 4-chlorobenzylamine (0.59 ml). The resulting crude solid is triturated with methanol and filtered. The light orange solid is recrystallized first from ethyl acetate/methyl t-butyl ether (5/1) and then from 50% methanol/dichloromethane to afford 0.310 g (52%) of the title compound as a peach-colored solid. Physical characteristics: M.p. 176–179° C.; ¹H NMR (300 MHz, DMSO-d₆) δ 10.34, 8.58, 8.28), 8.14, 8.04, 7.74–7.66, 7.47, 7.43–7.35, 7.04, 4.57, 3.60, 3.57, 2.; 13C NMR (75 MHz, CDCl₃) δ 177.2, 165.2, 147.6, 141.8, 140.0, 139.7, 136.7, 136.4, 133.2, 132.0, 129.4, 129.4, 129.1, 127.3, 127.0, 118.3, 112.6, 95.2, 67.35, 62.9, 53.9, 43.0; IR (drift) 1667, 1601, 1570, 1542, 1488, 1467, 1347, 1330, 1322, 1239, 1116, 865, 809, 797, 706 cm⁻¹; MS (ESI+) in/z 614 (M+H)+. Anal. Calcd for $C_{28}H_{25}ClIN_3O_3$: C, 54.78; H, 4.11; N, 6.84; Cl, 5.78. Found: C, 54.41; H, 4.15; N, 6.78; Cl, 5.70.

EXAMPLE 4

N-(4-Chlorobenzyl)-1-(4-chlorophenyl)-6-(4-morpholinylmethyl)-4-oxo-1,4-dihydro-3-quinolinecarboxamide [A.5, W=morpholinylmethyl, aryl =4-chlorophenyl, X=Cl.

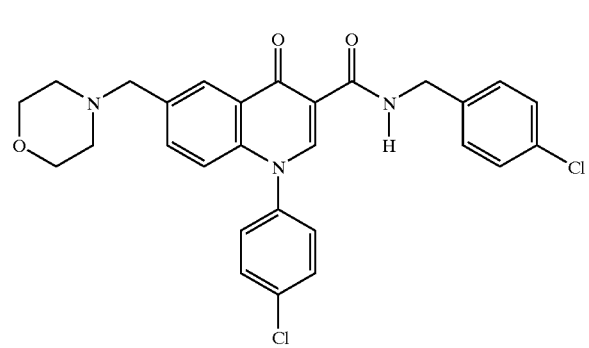

The title compound is prepared according to general preparation A.5 employing the product of Preparation 6d (0.50 g) and 4-chlorobenzylamine (0.77 mL). The resulting crude solid is filtered and recrystallized first from methanol and then from isopropanol to afford 0.330 g (50%) of the title compound as an off-white solid. Physical characteristics: M.p. 189–191° C.; ¹H NMR (300 MHz, DMSO-d₆) δ 10.35, 8.59, 8.28, 7.78–7.71, 7.67, 7.43–7.34, 7.07, 4.57, 3.61, 3.56, 2.36; ¹³C NMR (75 MHz, CDCl₃) δ 177.2, 165.2, 147.7, 140.1, 139.4, 137.7, 136.7, 134.3, 133.3, 131.1, 129.4, 129.0, 127.3, 118.215, 112.6, 67.3, 62.9, 53.9, 43.0; IR (drift) 1663, 1603, 1570, 1549, 1545, 1489, 1353, 1323, 1240, 1114, 1089, 1015, 864, 836, 809 cm-; HRMS (FAB) calcd for $C_{28}H_{25}CL_2N_3O_3$+H m/z 522.1351, found 522.1339. Anal. Calcd for $C_{28}H_{25}Cl_2N_3O_3$: C, 64.37; H, 4.82; N, 8.04; Cl, 13.57. Found: C, 64.24; H, 4.82; N, 8.00; Cl, 13.39.

EXAMPLE 5

N-(4-Chlorobenzyl)-1-(4-isopropylphenyl)-6-(4-morpholinylmethyl)-4-oxo-1,4-dihydro-3-quinolinecarboxamnide [A.5, W=morpholinylmethyl, aryl =4-isopropyl-phenyl, X=Cl.

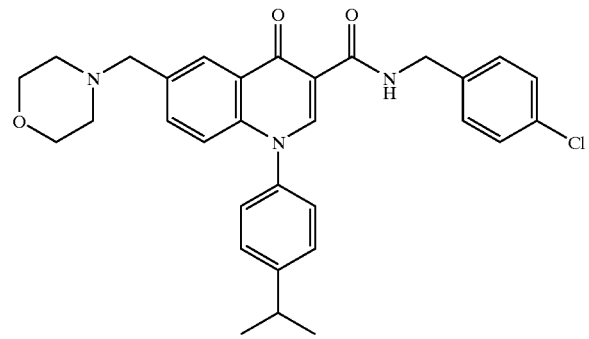

The title compound is prepared according to general preparation A.5 employing the product of Preparation 6e (0.50 g) and 4-chlorobenzylamine (0.70 mL). The reaction mixture is triturated with methanol and filtered to afford a tan powder. The product is recrystallized from isopropanol to afford 0.222 g (36%) of the title compound as an off-white powder. Physical characteristics: M.p. 199–203° C.; $^1$H NMR (300 MHz, DMSO-$d_6$) δ 10.37, 8.57, 8.28, 7.67, 7.56, 7.39, 7.06, 4.57, 3.60, 3.57, 3.11–3.01, 2.36, 1.3; $^{13}$C NMR (75 MHz, CDCl$_3$) δ 177.2, 165.5, 151.6, 148.1, 140.5, 138.7, 137.9, 136.0, 134.0, 133.2, 129.4, 129.1, 128.7, 127.4, 127.1, 118.7, 112.2,67.4,63.0, 53.9, 43.0, 34.4, 24.3; IR (drift) 2957, 2930, 1671, 1598, 1573, 1545, 1510, 1488, 1349, 1317, 1114, 863, 849, 838, 809 cm$^{-1}$; MS (ESI+) m/z 530 (M+H)+. Anal. Calcd for $C_{31}H_{32}ClN_3O_3$: C, 70.24; H, 6.09; N, 7.93; Cl, 6.69. Found: C, 70.06; H, 6.12; N, 7.87; Cl, 6.67.

EXAMPLE 6

N-(4-Chlorobenzyl)-1-(4-methoxyphenyl)-6-(4-morpholinylmethyl)-4-oxo-1,4-dihydro-3-quinolinecarboxamide [A.5, W=morpholinylmethyl, aryl =4-methoxy-phenyl, X=Cl.

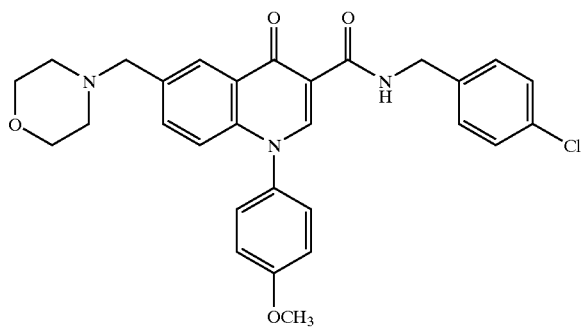

The title compound is prepared according to general preparation A.5 employing the product of Preparation 6f (0.50 g) and 4-chlorobenzylamine (0.72 mL). The reaction mixture is triturated with methanol and filtered to afford a peach powder. The product is recrystallized from isopropanol followed by ethanol to afford 0.266 g (44%) of the title compound as an off-white powder. Physical characteristics: M.p. 189–191° C.; $^1$H NMR (300 MHz, DMSO-$d_6$) δ 10.38, 8.56, 8.28, 7.67, 7.6, 7.39, 7.20, 7.05, 4.57, 3.88, 3.61, 3.57, 2.37; $^{13}$C NMR (75 MHz, CDCl$_3$) δ 177.2, 165.5, 148.3, 137.9, 136.0, 134.0, 129.4, 129.1, 128.8, 127.1, 118.6, 115.7, 112.2, 67.4, 63.0, 56.1, 53.9, 43.0; IR (drift) 1666, 1598, 1581, 1549, 1511, 1488, 1351, 1302, 1250, 1237, 1113, 865, 840, 809, 793 cm-; MS (ESI+) m/z 518 (M+H)$^+$. Anal. Calcd for $C_{29}H_{28}ClN_3O_4$: C, 67.11; H, 5.46; N, 8.10; Cl, 6.83. Found: C, 67.00; H, 5.48; N, 8.15; Cl, 6.84.

EXAMPLE 7

N-(4-Fluorobenzyl)-1-(4-chlorophenyl)-6-(4-morpholinylmethyl)-4-oxo-1,4-dihydro-3-quinolinecarboxamide [A.5, W=morpholinylmethyl, aryl=4-chlorophenyl, X=F

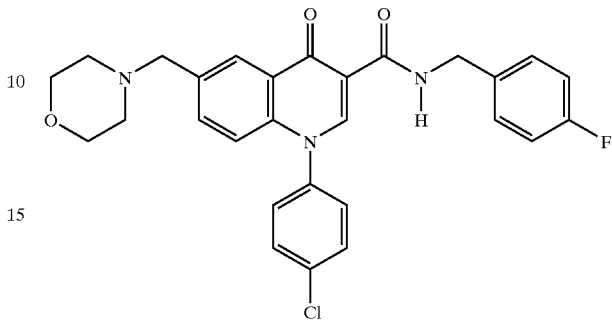

The title compound is prepared according to general preparation A.5 employing the product of Preparation 6d (0.50 g) and 4-fluorobenzylamine (0.77 mL). The resulting crude solid is filtered and recrystallized from methanol to afford 0.060 g (16%) of the title compound as an orange solid. Physical characteristics: M.p. 130–133° C.; 1H NMR (300 MHz, DMSO-$d_6$) δ 10.35, 8.59, 8.28, 7.78–7.72, 7.68–7.66, 7.41–7.38, 7.18, 7.07, 4.57, 3.61, 3.56, 2.36; $^3$C NMR (75 MHz, CDCl$_3$) δ 165.2, 147.7, 139.4, 137.7, 136.7, 134.2, 131.1, 129.7, 129.6, 129.0, 127.3, 118.2, 115.8, 115.7, 67.3, 62.9, 53.9,43.0;IR(drift) 1656, 1601, 1577, 1545, 1512, 1488(s), 1353, 1323, 1223, 1113, 863, 849, 834, 825, 811 cm-; MS (ESI+) r/z 447 (M+H)+. Anal. Calcd for $C_{28}H_{25}ClFN_3O_3$: C, 66.47; H, 4.98; N, 8.31; Cl, 7.01; F, 3.76. Found: C, 66.30; H, 5.06; N, 8.31; Cl, 6.98; F, 3.85.

EXAMPLE 8

N-(4-Chlorobenzyl)-1-(2-(hydroxymethyl)phenyl)-6-(4-morpholinylmethyl)-4-oxo-1,4-dihydro-3-quinolinecarboxamide [A.5, W=morpholinylmethyl, aryl =2-hydroxy-methylphenyl, X=Cl.

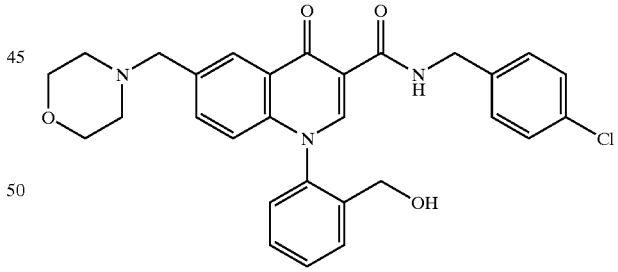

The title compound is prepared according to general preparation A.5 employing the product of Preparation 6g (0.42 g) and 4-chlorobenzylamine (0.62 mL). The crude product is purified by column chromatography (CH$_2$Cl$_2$/methanol, 100/1; 50/1; 25/1) and then is triturated (diethyl ether) to afford 0.37 g (72%) of the title compound as a light yellow solid. Physical characteristics: M.p. 162–163° C.; $^1$H NMR (400 MHz, DMSO-$d_6$) δ 10.37, 8.57, 8.30, 7.75–7.57, 7.43–7.35, 6.83, 5.24, 4.60, 4.55, 4.16, 3.61, 3.57, 2.37; $^{13}$C NMR (100 MHz, DMSO-$d_6$) δ 176.7, 164.9, 148.6, 140.4, 139.9, 139.4, 138.9, 136.2, 135.0, 132.3, 131.4, 130.4, 130.1, 130.0, 129.2, 129.0, 127.1, 126.6, 118.8, 111.9, 67.0, 62.5, 59.8, 54.0, 42.3; IR (diffuse reflectance) 1662 (s), 1601, 1569, 1550 (s), 1488 (s), 1348, 1328, 1319, 1246, 1109, 1009, 869, 810, 796, 782 cm$^{-1}$; MS (ESI+) 1n/z 518 (100, (M+H)+), 519 (32), 520 (37). Anal. Calcd for $C_{29}H_{28}ClN_3O_4$: C, 67.24; H, 5.45; N, 8.11; Cl, 6.84. Found: C, 66.85; H, 5.49; N, 7.99; Cl, 7.01.

EXAMPLE 9

N-(4-Chlorobenzyl)-1-(2,3-dihydro-1H-inden-5-yl)-6-(4-morpholinylmethyl)-4-oxo-1,4-dihydro-3-quinolinecarboxamide [A.5, W=morpholinylmethyl, aryl =indan, X=Cl

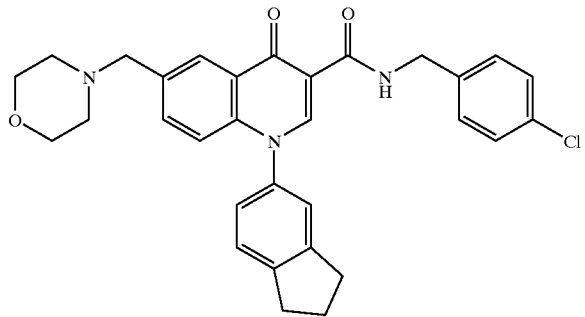

The title compound is prepared according to general preparation A.5 employing the product of Preparation 6h (0.43 g) and 4-chlorobenzylamine (0.62 mL). The crude product is diluted with methanol (5 mL), filtered, and recrystallized from ethanol to afford 0.268 g (49%) of the title compound as a white solid. Physical characteristics: M.p. 123–125° C.; $^1$H NMR (400 MHz, DMSO-d$_6$) δ 10.38, 8.57, 8.29, 7.67, 7.51, 7.43–7.36, 7.09, 4.58, 3.61, 3.57, 2.99, 2.37, 2.13; $^3$C NMR (100 MHz, DMSO-d$_6$) δ 176.1, 164.4, 147.8, 146.6, 146.2, 140.2, 139.1, 139.0, 135.6, 134.3, 131.8, 129.5, 128.7, 126.6, 126.1, 126.0, 125.5, 123.6, 118.9, 111.2, 66.5, 62.0, 53.4, 41.8, 32.7, 32.5, 25.6; IR (diffuse reflectance) 2949 (w), 2854 (w), 1661, 1599, 1577, 1543, 1537, 1487 (s), 1357, 1331, 1321, 1115, 865 (w), 832 (w), 809 cm$^{-1}$; MS (ESI+) m/z 528 (100, (M+H)$^+$), 529 (40), 530 (40), 531 (10). Anal. Calcd for $C_{31}H_{30}ClN_3O_3$: C, 70.51; H, 5.73; N, 7.96; Cl, 6.71. Found: C, 70.23; H, 5.72; N, 7.90; Cl, 6.68.

EXAMPLE 10

1-(1,3-Benzodioxol-5-yl)-N-(4-chlorobenzyl)-6-(4-morpholinylmethyl)-4-oxo-1,4-dihydro-3-quinolinecarboxamide [A.5, W=morpholinylmethyl, aryl =3,4-methylene-dioxyphenyl, X=Cl

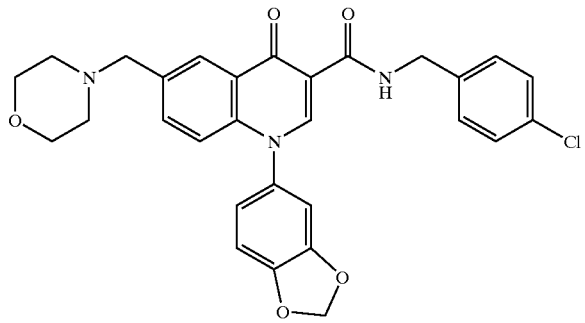

The title compound is prepared according to general preparation A.5 employing the product of Preparation 6i (0.436 g) and 4-chlorobenzylamine (0.62 mL). The crude product is diluted with methanol (5 mL), filtered, and recrystallized from ethanol to afford 0.185 g (35%) of the title compound as a gray solid. Physical characteristics: M.p. 188–189° C.; $^1$H NMR (300 MHz, DMSO-d$_6$) δ 10.37, 8.57, 8.28, 7.68, 7.43–7.34, 7.19–7.12, 6.21, 4.57, 3.61, 3.57, 2.37; $^{13}$C NMR (100 MHz, DMSO-d$_6$) δ 176.1, 164.4, 148.7, 148.0, 140.4, 139.0, 135.6, 134.5, 134.3, 131.8, 129.5, 128.7, 126.6, 126.0, 121.6, 118.9, 111.2, 109.3, 108.8, 102.7, 66.5, 62.0, 53.4, 41.8; IR (diffuse reflectance) 1664, 1597, 1572, 1545, 1486 (s), 1316 (w), 1249, 1221, 1208, 1115, 1035, 868, 826 (w), 815 (w), 808 cm-; MS (ESI+) m/z 532 (100, (M+H)+), 533 (37), 534 (42), 535 (9). Anal. Calcd for $C_{29}H_{26}ClN_3O$ $O_5$: C, 65.47; H, 4.93; N, 7.90; Cl, 6.66. Found: C, 65.07; H, 4.97; N, 7.83; Cl, 6.99.

EXAMPLE 11

N-(4-Chlorobenzyl)-1-(1H-indol-5-yl)-6-(4-morpholinylmethyl)-4-oxo-1,4-dihydro-3-quinolinecarboxamide [A.5, W=morpholinylmethyl, aryl =5-indole, X=Cl.

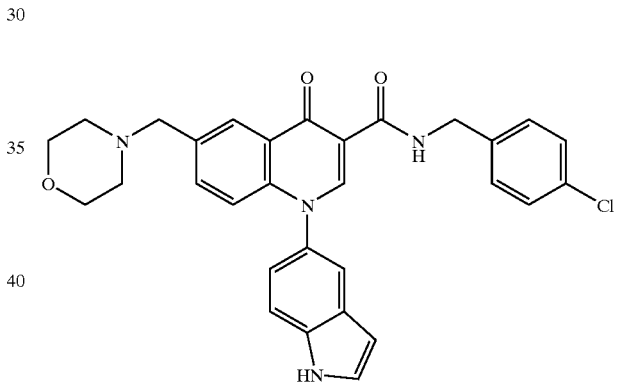

The title compound is prepared according to general preparation A.5 employing the product of Preparation 6j (0.43 g) and 4-chlorobenzylamine (0.62 mL). The crude product is diluted with methanol (5 mL) and filtered to afford 0.438 g (83%) of the title compound as a white solid. Physical characteristics: M.p. 241–243° C.; $^1$H NMR (300 MHz, DMSO-d$_6$) δ 11.57, 10.43, 8.66, 8.29, 7.84, 7.64, 7.58-, 7.45–7.36, 7.28, 7.07, 6.58, 4.58, 3.60, 3.57, 2.37; $^{13}$C NMR (100 MHz, DMSO-d$_6$) δ 176.1, 164.6, 148.3, 140.8, 139.0, 136.2, 135.5, 134.1, 132.8, 131.8, 129.5, 129.2, 128.7, 128.4, 128.3, 126.6, 125.9, 120.0, 119.2, 113.1, 111.0, 102.3, 66.5, 62.0, 53.4, 41.8; IR (diffuse reflectance) 3175, 3154 (b), 3066 (w), 1651, 1600, 1550 (s), 1488 (s), 1456, 1346, 1315, 1233, 1116, 864, 805, 799 cm$^{-1}$; MS (ESI+) m/z 527 (100, (M+H)+), 528 (41), 529 (37), 530 (9). Anal. Calcd for $C_{30}H_{27}ClN_4O_3$: C, 68.37; H, 5.16; N, 10.63; Cl, 6.73. Found: C, 68.11; H, 5.22; N, 10.46; Cl, 7.29.

EXAMPLE 12

N-(4-Fluorobenzyl)-1-(1 H-indol-5-yl)-6-(4-morpholinylmethyl)-4-oxo-1,4-dihydro-3-quinolinecarboxamide [A.5, W=morpholinylmethyl, aryl =5-indole, X=F.

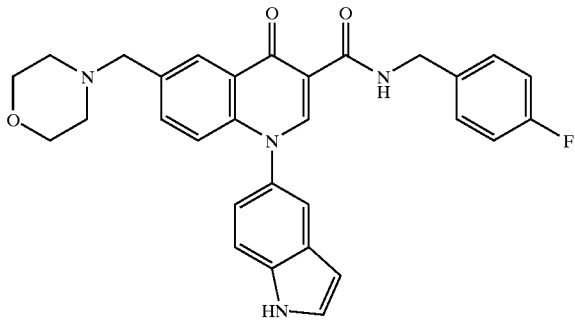

The title compound is prepared according to general preparation A.5 employing the product of Preparation 6j (0.43 mg) and 4-fluorobenzylamine (0.57 mL). The crude product is crystallized from diethyl ether/EtOAc/hexane to afford 0.412 mg (81%) of the title compound as a white solid. Physical characteristics: M.p. 223–225° C.; $^1$H NMR (400 MHz, DMSO-$d_6$) δ 11.57, 10.41, 8.66, 8.29, 7.84, 7.65, 7.64, 7.41, 7.28, 7.18, 7.07, 6.59, 4.57, 3.60, 3.56, 2.37; $^{13}$C NMR (100 MHz, DMSO-$d_6$) δ 176.7, 165.0, 162.1 (d, J =242 Hz), 148.9, 141.4, 136.7, 136.6 (d, J =3 Hz), 136.0, 134.7, 133.4, 130.2 (d, J =8 Hz), 128.9, 128.8, 127.2, 126.5, 120.5, 119.7, 116.0 (d, J =21 Hz), 113.6, 111.6, 102.9, 67.1, 62.6, 54.0, 45.1; IR (diffuse reflectance) 3176, 3156 (b), 3066, 2932, 1651, 1601, 1568, 1551, 1508, 1487, 1456, 1346, 1232, 1219, 1117 cm$^{-1}$; MS (ESI+) m/z 511 (100, (M+H)+), 512 (31). Anal. Calcd for $C_{30}H_{27}FN_4O_3$: C, 70.57; H, 5.33; N, 10.97; F, 3.72. Found: C, 70.30; H, 5.44; N, 10.76; F, 4.15.

EXAMPLE 13

N-(4-Chlorobenzyl)-1-(3-hydroxyphenyl)-6-(4-morpholinylmethyl)-4-oxo-1,4-dihydro-3-quinolinecarboxamide [A.5, W=morpholinylmethyl, aryl =3-hydroxy-phenyl, X=Cl.

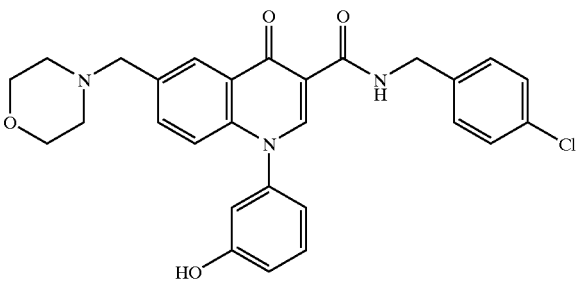

The title compound is prepared according to general preparation A.5 employing the product of Preparation 6k (0.41 g) and 4-chlorobenzylamine (0.62 mL). The mixture is diluted with methanol (5 mL), poured into saturated aqueous NH$_4$Cl, and filtered. The crude product is purified by column chromatography (CH$_2$Cl$_2$/methanol, 50/1; 33/1) and crystallization from diethyl ether/EtOAc to afford 0.24 g (48%) of the title compound as a white solid. Physical characteristics: M.p. 248–250° C.; $^1$H NMR (400 MHz, DMSO-$d_6$) δ 10.37, 10.18, 8.57, 8.28, 7.69, 7.47, 7.43–7.35, 7.14, 7.06, 7.00, 4.57, 3.61, 3.57, 2.37; $^3$C NMR (75 MHz, DMSO-$d_6$) δ 175.5, 164.0, 158.8, 147.1, 141.4, 139.5, 138.6, 135.3, 133.9, 131.4, 131.1, 129.2, 128.3, 126.3, 125.6, 118.4, 117.5, 117.1, 114.1, 110.8, 66.2, 61.6, 53.1, 41.5; IR (diffuse reflectance) 3062, 3046 (b), 1647 (s), 1603, 1551 (s), 1488 (s), 1347, 1330, 1312, 1223, 1209, 1119, 871, 816, 806 cm$^{-1}$; MS (ESI+) m/z 504 (100, (M+H)$^+$), 505 (37), 506 (42), 507 (13); Anal. Calcd for $C_{28}H_{26}ClN_3O_4$: C, 66.73; H, 5.20; N, 8.34; Cl, 7.03. Found: C, 66.62; H, 5.31; N, 8.21; Cl, 6.96.

EXAMPLE 14

N-(4-Chlorobenzyl)-1-(3-(2-hydroxyethyl)phenyl)-6-(4-morpholinylmethyl)-4-oxo-1,4-dihydro-3-quinolinecarboxamide [A.5, W=morpholinylmethyl, aryl =3-(2-hydroxyethyl)-phenyl, X=Cl.

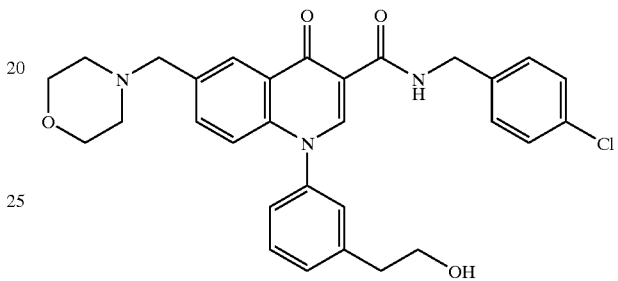

The title compound is prepared according to general preparation A.5 employing the product of Preparation 61 (0.436 g) and 4-chlorobenzylamine (0.62 mL). The crude product is crystallized from diethyl ether/EtOAc/hexane to afford 0.412 g (78%) of the title compound as a white solid. Physical characteristics: M.p. 158–160° C.; H NMR (400 MHz, DMSO-$d_6$) δ 10.37, 8.59, 8.30, 7.68, 7.59, 7.53–7.48, 7.43–7.36, 7.09, 4.70, 4.58, 3.68, 3.61, 3.57, 2.84, 2.37; $^3$C NMR (100 MHz, DMSO-$d_6$) δ 175.7, 164.1, 147.4, 142.5, 140.3, 139.6, 138.6, 135.4, 134.0, 131.4, 130.6, 130.0, 129.2, 128.4, 127.7, 126.3, 125.7, 124.8, 118.4, 110.9, 66.2, 61.6, 53.1, 41.5, 38.5; IR (diffuse reflectance) 3364, 3242, 2858, 1663 (s), 1599, 1568, 1549, 1537 (s), 1487 (s), 1347, 1330, 1322, 1113, 817, 809 cm-l; MS (ESI+) m/z 532 (100, (M+H)+), 533 (410), 534 (38); Anal. Calcd for $C_{30}H_{30}ClN_3O_4$: C, 67.73; H, 5.68; N, 7.90; Cl, 6.66. Found: C, 67.48; H, 5.72; N, 7.87; Cl, 6.70.

EXAMPLE 15

N-(4-Fluorobenzyl)-1-(3-(2-hydroxyethyl)phenyl)-6-(4-morpholinylmethyl)-4-oxo-1,4-dihydro-3-quinolinecarboxamide [A.5, W=morpholinylmethyl,-aryl =3-(2-hydroxyethyl)-phenyl, X=F

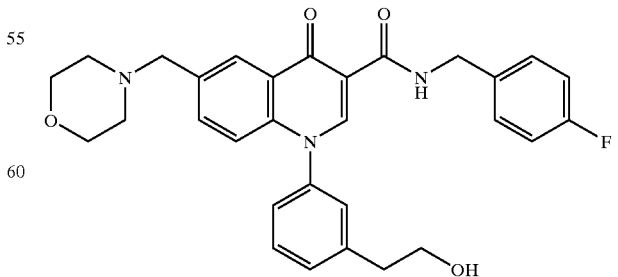

The title compound is prepared according to general preparation A.5 employing the product of Preparation 61

(0.436 mg) and 4-fluorobenzylamine (0.57 mL). The crude product is crystallized (methanol/Et₂O/hexane; EtOAc/hexane), purified by column chromatography (CH₂Cl₂/methanol, 50/1; 33/1, 25/1), and crystallized (Et₂O/EtOAc) to afford 0.271 mg (53%) of the title compound as a white solid. Physical characteristics: M.p. 128–132° C.; $^1$H NMR (300 MHz, DMSO-$d_6$) δ 10.35, 8.59, 8.29, 7.68, 7.62–7.47, 7.39, 7.18, 7.09, 4.70, 4.57, 3.69, 3.61, 3.57, 2.84, 2.37; $^{13}$C NMR (100 MHz, DMSO-$d_6$) δ 176.1, 164.3, 161.6 (d, J=242 Hz), 147.7, 142.9, 140.7, 140.0, 136.0 (d, J =3 Hz), 135.7, 134.3, 131.0, 130.3, 129.7 (d, J =8 Hz), 128.0, 126.6, 126.1, 125.1, 118.8, 115.5 (d, J=21 Hz), 111.3, 66.5, 61.9, 53.4, 41.8, 38.9; IR (diffuse reflectance) 1658 (s), 1601, 1574, 1569, 1545 (s), 1511, 1487 (s), 1355, 1323, 1246, 1221, 1113, 863, 832, 811 cm$^{-1}$; MS (ESI+) m/z 516 (100, (M+H)$^+$), 517 (36); HRMS (FAB) calcd for $C_{30}H_{30}FN_3O_4$+H m/z 516.2299, found 516.2292. Anal. Calcd for $C_{30}H_{30}FN_3O_4$: C, 69.89; H, 5.86; N, 8.15. Found: C, 69.73; H, 6.05; N, 8.02.

EXAMPLE 16

N-(4-Chlorobenzyl)-1-(3-methoxyphenyl)-6-(4-morpholinylmethyl)-4-oxo-1,4-dihydro-3-quinolinecarboxamide [A.5, W=morpholinylmethyl, aryl =3-methoxy-phenyl, X=Cl.

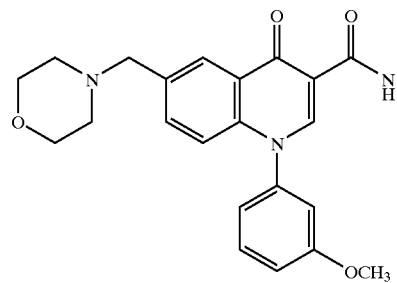

The title compound is prepared according to general preparation A.5 employing the product of Preparation 6m (0.50 g) and 4-chlorobenzylamine (0.72 mL). The crude product is triturated with methanol, filtered, and recrystallized (methanol) to afford 0.21 g (34%) of the title compound as a white solid. Physical characteristics: M.p. 110–113° C.; $^1$H NMR (400 MHz, DMSO-$d_6$) δ 10.38, 8.59, 8.28, 7.68, 7.60, 7.43–7.35, 7.33, 7.25–7.21, 7.10, 4.58, 3.83, 3.61, 3.57, 2.38; $^{13}$C NMR (100 MHz, CDCl₃) δ 177.2, 165.4, 161.4, 147.8, 141.9, 140.2, 137.828, 136.0, 134.1, 133.2, 131.5, 129.4, 127.3, 119.6, 118.6, 116.3, 113.2, 112.2, 67.4, 63.0, 56.1, 53.9, 43.0; IR (diffuse reflectance) 1666 (s), 1603, 1578, 1546 (s), 1489 (s), 1457, 1351, 1333, 1325, 1318, 1221, 1118, 868, 808, 710 cm-; MS (ESI) 518.0 (M+H)+. Anal. Calcd for $C_{29}H_{28}ClN_3O_4$: C, 67.24; H, 5.45; N, 8.11; Cl, 6.84. Found: C, 67.24; H, 5.45; N, 8.17.

EXAMPLE 17

N-(4-Chlorobenzyl)-1-(3-(hydroxymethyl)phenyl)-6-(4-morpholinylmethyl)-4-oxo-1,4-dihydro-3-quinolinecarboxamide [A.5, W=morpholinylmethyl, aryl =3-hydroxymethylphenyl, X=Cl.

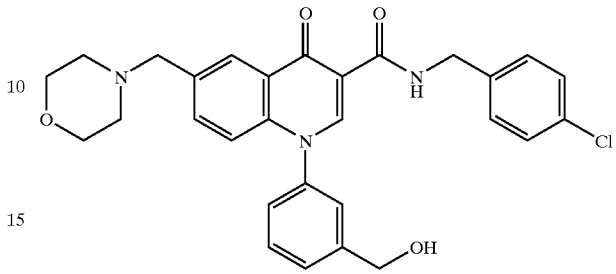

The title compound is prepared according to general preparation A.5 employing the product of Preparation 6n (0.225 g) and 4-chlorobenzylamine (0.36 mL). The crude product is triturated with methanol, filtered, and recrystallized (methanol) to afford 83 mg (27%) of the title compound as a white solid. Physical characteristics: M.p. 119–121° C.; $^1$H NMR (400 MHz, DMSO-$d_6$) δ 10.38, 8.59, 8.29, 7.70–7.52, 7.40, 7.08, 5.41, 4.62, 4.57, 3.61, 3.57, 2.38; IR (diffuse reflectance) 1662 (s), 1600, 1545 (s), 1489 (s), 1354, 1348, 1333, 1326, 1115, 861, 810, 798, 789, 713, 704 cm$^{-1}$; HRMS (FAB) calcd for $C_{29}H_{28}ClN_3O_4$+H m/z 518.1846, found 518.1837.

EXAMPLE 18

N-(4-Chlorobenzyl)-6-(4-morpholinylmethyl)-1-(4-(4-morpholinyl)phenyl)-4-oxo-1,4-dihydro-3-quinolinecarboxamide [A.5, W=morpholinylmethyl, aryl =4-morpholinylphenyl, X=Cl.

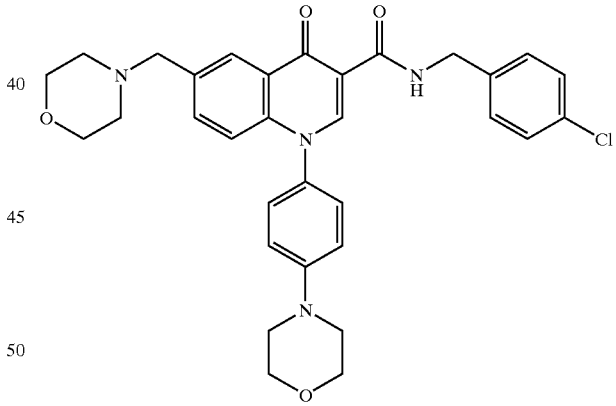

The title compound is prepared according to general preparation A.5 employing the product of Preparation 6o (0.500 g) and 4-chlorobenzylamine (0.61 mL). The crude product is triturated with methanol, filtered, and recrystallized (methanol) to afford 280 mg (49%) of the title compound as a yellow solid. Physical characteristics: M.p. 162–164° C.; $^1$H NMR (400 MHz, DMSO-$d_6$) δ 10.40, 8.55, 8.28, 7.68, 7.48, 7.39, 7.17, 7.09, 4.57, 3.78, 3.61, 3.57, 3.27, 2.37; IR (diffuse reflectance) 1659 (s), 1608, 1591, 1549, 1543, 1515 (s), 1487 (s), 1351, 1330, 1317, 1241, 1124, 1114, 926, 808 cm$^{-1}$; HRMS (FAB) calcd for $C_{32}H_{33}ClN_4O_4$+H m/z 573.2268, found 573.2264. Anal. Calcd for $C_{32}H_{33}ClN_4O_4$: C, 67.07; H, 5.80; N, 9.78; Cl, 6.19. Found: C, 66.89; H, 5.76; N, 9.69; Cl, 6.31.

EXAMPLE 19

N-(4-Chlorobenzyl)-1-(3,4-difluorophenyl)-6-(4-morpholinylmethyl)-4-oxo-1,4-dihydro-3-quinolinecarboxamide [A.5, W=morpholinylmethyl, aryl =3,4-difluorophenyl, X=Cl.

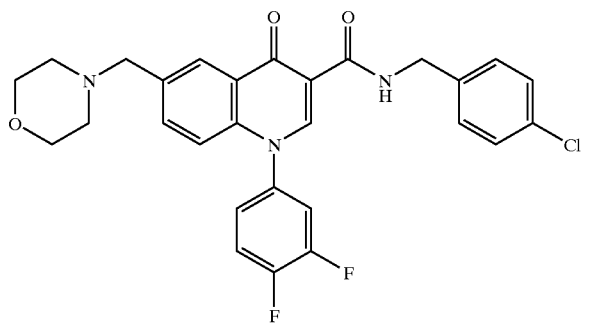

The product of Preparation 6p (0.500 mg) is suspended in a mixture of THF and methanol (7 mL, 1/1). An aqueous solution of 1 M LiOH (3.5 mL) is added dropwise and the mixture is stirred at 40° C. for 3 h. The reaction mixture is then cooled to room temperature and conc. HCl is added dropwise to afford 0.29 g (62%) of the corresponding carboxylic acid as a white precipitate. The resulting crude carboxylic acid (0.25 g) is dissolved in DMF (6 mL) and 1,1'-carbonyldiimidazole (0.107 g) is added. The reaction mixture is heated to 60° C. for 18 h, 4-chlorobenzylamine (0.10 mL) is added, and the mixture is stirred at room temperature for an additional 8 h. The mixture is poured into water. The crude product is filtered and recrystallized from methanol to afford 0.120 g (34%) of the title compound as a white solid. Physical characteristics: M.p 107–110° C.; $^1$H NMR (400 MHz, DMSO-$d_6$) δ 10.35, 8.63, 8.28, 8.05–7.98, 7.78, 7.68, 7.65–7.60, 7.39, 7.12, 4.59, 3.61, 3.57, 2.38; IR (diffuse reflectance) 1663 (s), 1601, 1578, 1550, 1534, 1513 (s), 1490, 1360, 1326 (w), 1274, 1215, 1118, 867 (w), 823 (w), 808 cm-; HRMS (FAB) calcd for $C_{28}H_{24}ClF_2N_3O_3$+H m/z 524.1552, found 524.1556. Anal. Calcd for $C_{28}H_{24}ClF_2N_3O_3$ 0.36 $H_2O$: C, 63.40; H, 4.70; N, 7.92; Cl, 6.68; F, 7.16. Found: C, 63.38; H, 4.89; N, 7.67; Cl, 6.47; F, 7.07.

General Preparation H.2 A mixture of N-(4-chlorobenzyl)-1-(3-iodophenyl)-6-(4-morpholinylmethyl)-4-oxo-1,4-dihydro-3-quinolinecarboxamide (Example 3), $Pd(PPh_3)_2Cl_2$ (0.05 equiv), CuI (0.3 equiv), and an acetylene (1.2 equiv) are dissolved in diethylamine and stirred at room temperature for 18 h. The reaction mixture is concentrated in vacuo. The crude product is purified by either recrystallization or column chromatography to afford the desired product H.2. The following compounds (Examples 20–22) are prepared according to these procedures.

EXAMPLE 20

N-(4-Chlorobenzyl)-1-(3-(3-hydroxy-1-propynyl)phenyl)-6-(4-morpholinylmethyl)-4-oxo-1,4-dihydro-3-quinolinecarboxamide [H.2, W=morpholinylmethyl, Z=hydroxymethyl, X=Cl.

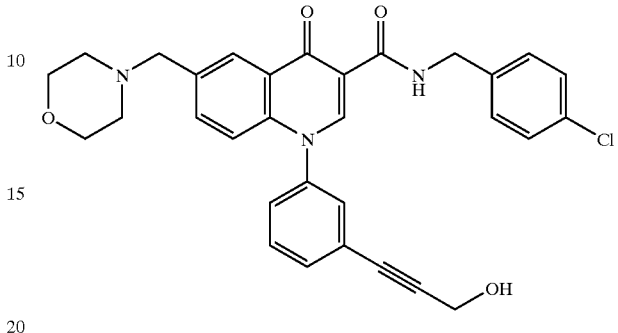

The title compound is prepared according to general preparation H.2 employing N-(4-chlorobenzyl)-1-(3-iodophenyl)-6-(4-morpholinylmethyl)-4-oxo-1,4-dihydro-3-quinolinecarboxamide (Example 3, 1.22 g), CuI (0.114 g), $Pd(PPh_3)_2Cl_2$ (0.070 g), and propargyl alcohol (0.166 mL) in diethylamine (24 mL). The crude product is purified by column chromatography ($CH_2Cl_2$/methanol, 99/1, 98/2, 97/3), triturated with $Et_2O$, and recrystallized from ethanol to afford 210 mg (19%) of the title compound as a beige powder. Physical characteristics: M.p. 145–148° C. $^1$H NMR (400 MHz, DMSO-$d_6$) δ 10.36, 8.59, 8.29, 7.78, 7.73–7.66, 7.42–7.36, 7.06, 5.42, 4.58, 4.33, 3.61, 3.57, 2.37; $^{13}$C NMR (75 MHz, CDCl$_3$) δ 176.8, 147.3, 140.6, 139.7, 137.3, 133.9, 130.5, 129.0, 128.7, 127.1, 126.9, 125.3, 118.0, 112.1, 90.2, 83.4, 66.9, 62.5, 53.5, 51.4, 42.7; IR (diffuse reflectance) 3391, 3242, 1665 (s), 1600, 1569, 1549, 1544 (s), 1487 (s), 1350, 1325, 1221, 1114, 1029, 816, 808 cm-; HRMS (FAB) calcd for $C_{31}H_{28}ClN_3O_4$+H m/z 542.1846, found 542.1855. Anal. Calcd for $C_{31}H_{28}ClN_3O_4$ 0.31 $H_2O$): C, 67.99; H, 5.27; N, 7.67; Cl, 6.47. Found: C, 67.97; H, 5.25; N, 7.61; Cl, 6.42.

EXAMPLE 21

N-(4-Chlorobenzyl)-1-(3-(4-hydroxy-1-butynyl)phenyl)-6-(4-morpholinylmethyl)-4-oxo-1,4-dihydro-3-quinolinecarboxamide [H.2, W=morpholinylmethyl, Z =2-hydroxyethyl, X=Cl.

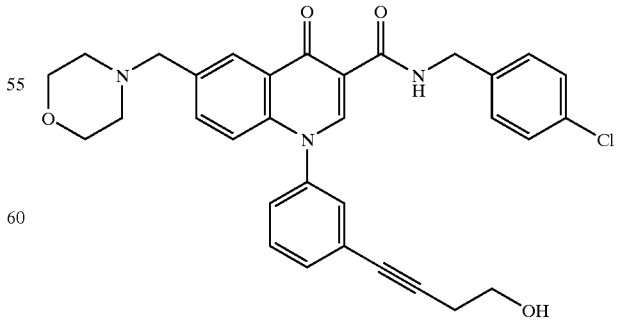

The title compound is prepared according to general preparation H.2 employing N-(4-chlorobenzyl)-1-(3- iodophenyl)-6-(4-morpholinylmethyl)-4-oxo-1,4-dihydro-3-quinolinecarboxamide (Example 3, 1.22 g), CuI (0.114 g), Pd(PPh$_3$)$_2$Cl$_2$ (0.070 g), and 3-butyn-1-ol (0.21 mL) in diethylamine (24 mL). The crude product is purified by column chromatography (CH$_2$Cl$_2$/methanol, 99/1, 9812, 97/3), triturated with Et$_2$O, and recrystallized from EtOAc followed by ethanol to afford 150 mg (13%) of the title compound as an off-white powder. Physical characteristics: M.p. 125–128 C. $^1$H NMR (400 MHz, DMSO-d$_6$) δ 10.36, 8.58, 8.28, 7.74, 7.69–7.63, 7.39, 7.05, 4.92, 4.59, 3.62–3.55, 2.58, 2.37; IR (diffuse reflectance) 1662 (s), 1598, 1578, 1574, 1569, 1550 (s), 1544 (s), 1487 (s), 1346, 1331, 1322, 1221, 1114, 809, 797 cm$^{-1}$; HRMS (FAB) calcd for C$_{32}$H$_{30}$ClN$_3$O$_4$+H m/z 556.2003, found 556.2017. Anal. Calcd for C$_{32}$H$_{30}$ClN$_3$O$_4$–0.45 H$_2$O: C, 68.12; H, 5.52; N, 7.45; Cl, 6.28. Found: C, 68.54; H, 5.49; N, 7.45; Cl, 6.28.

EXAMPLE 22

N-(4-Chlorobenzyl)-1-(3-(4-hydroxy-1-butynyl)phenyl)-6-(4-morpholinylmethyl)-4-oxo-1,4-dihydro-3-quinolinecarboxamide [H.2, W=morpholinylmethyl, Z=3-hydroxypropyl, X=Cl.

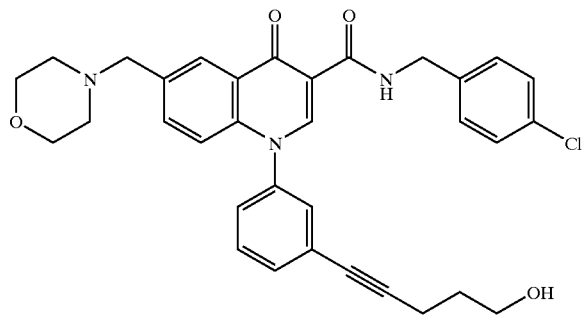

The title compound is prepared according to general preparation H.2 employing N-(4-chlorobenzyl)-1-(3-iodophenyl)-6-(4-morpholinylmethyl)-4-oxo-1,4-dihydro-3-quinolinecarboxamide (Example 3, 1.22 g), CuI (0.114 g), Pd(PPh$_3$)$_2$Cl$_2$ (0.070 g), and 4-pentyn-1-ol (0.26 mL) in diethylamine (24 mL). The crude product is purified by column chromatography (CH$_2$Cl$_2$/methanol, 99/1, 9812, 97/3, 95/5), triturated with Et$_2$O, and recrystallized from EtOAc to afford 407 mg (36%) of the title compound as an off-white powder. Physical characteristics: M.p. 125–128° C.; $^1$H NMR (300 MHz, DMSO-d$_6$) δ 10.36, 8.58, 8.29, 7.74, 7.69–7.63, 7.39, 7.05, 4.58–4.52, 3.62–3.55, 2.50, 2.37, 1.69; $^{13}$C NMR (75 MHz, CDCl$_3$) o 176.9, 164.9, 147.4, 140.6, 139.7, 137.4, 135.8, 133.8, 133.1, 132.8, 130.3, 129.0, 128.7, 126.9, 126.8, 126.5, 118.1, 112.0, 92.6, 79.2, 67.0, 62.6, 61.5, 53.6, 42.7, 31.2, 15.9; IR (diffuse reflectance) 3039, 2949, 2853, 1656 (s), 1600, 1569, 1550 (s), 1544, 1486 (s), 1359, 1348, 1322, 1221, 1114, 810 cm-; HRMS (FAB) calcd for C$_{33}$H$_{32}$ClN$_3$O$_4$+H m/z 570.2159, found 570.2150. Anal. Calcd for C$_{33}$H$_{32}$ClN$_3$O$_4$: C, 69.53; H, 5.66; N, 7.37; Cl, 6.22. Found: C, 69.56; H, 5.73; N, 7.31; Cl, 6.18.

General Preparation H.4 The corresponding alkynyl derivative H.2 (General Preparation H.2) is dissolved in methanol/CH$_2$Cl$_2$ (4/1) and added to 10% Pd/C. The reaction mixture is hydrogenated under 35 psi of hydrogen for 30 min-1 h, filtered through Celite, and then concentrated in vacuo. The crude product is purified by either recrystallization or column chromatography to afford the desired product H.4. The following compounds (Examples 23–25) are prepared according to these procedures.

EXAMPLE 23

N-(4-Chlorobenzyl)-1-(3-(5-hydroxypentyl)phenyl)-6-(4-morpholinylmethyl)-4-oxo-1,4-dihydro-3-quinolinecarboxamide [H.4, W=morpholinylmethyl, Z=5-hydroxypentyl, X=Cl.

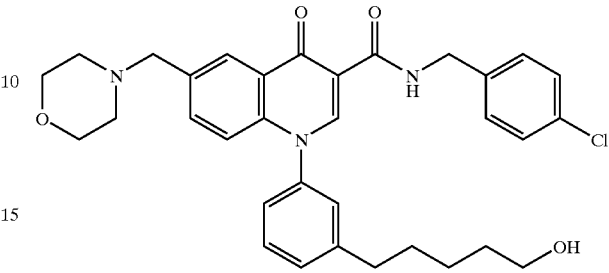

The title compound is prepared according to general preparation H.4 employing N-(4-chlorobenzyl)-1-(3-(4-hydroxy-1-butynyl)phenyl)-6-(4-morpholinylmethyl)-4-oxo-1,4-dihydro-3-quinolinecarboxamide (Example 22, 0.250 g) in a solution of methanol/CH$_2$Cl$_2$ (4/1, 50 mL) and 10% Pd/C (52 mg). The crude product is purified by column chromatography (CH$_2$Cl$_2$/methanol, 99/1, 98/2, 97/3, 95/5). The resulting solid is recrystallized from EtOAc/heptane to afford 53 mg (20%) of the title compound as a white solid. Physical characteristics: M.p. 142–144° C.; $^1$H NMR (400 MHz, DMSO-d$_6$) δ 10.38, 8.58, 8.29, 7.68, 7.58, 7.53–7.45, 7.43–7.35, 7.06, 4.58, 4.35, 3.61, 3.57, 3.41–3.35, 2.70, 2.37, 1.68–1.60, 1.49–1.40, 1.38–1.30; IR (diffuse reflectance) 2949 (w), 2931, 2855, 1656 (s), 1600, 1544, 1488 (s), 1456, 1360, 1321, 1113, 863, 834 (w), 810, 712 (w) cm-. Anal. Calcd for C$_{33}$H$_{36}$ClN$_3$O$_4$: C, 69.04; H, 6.32; N, 7.32; Cl, 6.18. Found: C, 69.32; H, 6.46; N, 7.23; Cl, 5.27.

EXAMPLE 24

N-(4-Chlorobenzyl)-1-(3-(4-hydroxybutyl)phenyl)-6-(4-morpholinylmethyl)-4-oxo-1,4-dihydro-3-quinolinecarboxamide [H.4, W=morpholinylmethyl, Z=4-hydroxybutyl, X=Cl.

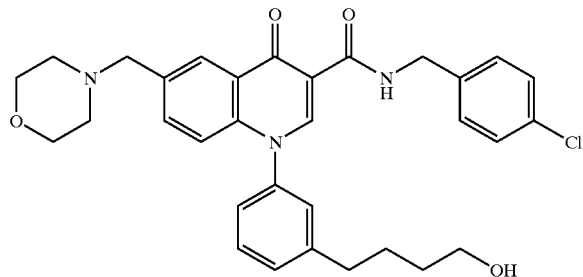

The title compound is prepared according to general preparation H.4 employing N-(4-chlorobenzyl)-1-(3-(4-hydroxy-1-butynyl)phenyl)-6-(4-morpholinylmethyl)-4-oxo-1,4-dihydro-3-quinolinecarboxamide (Example 21, 0.300 g) in a solution of methanol/CH$_2$Cl$_2$ (4/1, 50 mL) and 10% Pd/C (52 mg). The crude product is purified by column chromatography (CH$_2$Cl$_2$/methanol, 98/2, 97/3, 95/5). The resulting solid is recrystallized from methanol to afford 83 mg (27%) of the title compound as a white solid. Physical characteristics: M.p. 119–121° C.; $^1$H NMR (300 MHz, DMSO-d$_6$) δ 10.36, 8.58, 8.29, 7.68, 7.58, 7.53–7.45, 7.43–7.35, 7.06, 4.58, 4.35, 3.60–3.55, 3.41, 2.70, 2.37, 1.68–1.60, 1.49–1.40; $^{13}$C NMR (75 MHz, CDCl$_3$) δ 176.8, 165.1, 145.4, 140.7, 140.0, 137.5, 135.7, 133.7, 130.2, 129.0, 128.7, 127.0, 126.8, 124.5, 118.3, 118.3, 111.8, 67.0, 62.6, 53.6, 42.6, 35.4, 32.2, 27.4; IR (diffuse reflectance) 3225, 2956, 2941, 2921, 2863, 1663 (s), 1601, 1579, 1549 (s), 1543 (s), 1488 (s), 1354, 1329, 1322, 1114 cm$^{-1}$; HRMS (FAB) calcd for $C_{32}H_{34}ClN_3O_4$+H m/z 560.2316, found 560.2320. Anal. Calcd for $C_{32}H_{34}ClN_3O_4$: C, 68.62; H, 6.12; N, 7.50; Cl, 6.33. Found: C, 68.36; H, 6.18; N, 7.46; Cl, 5.90.

EXAMPLE 25

N-(4-Chlorobenzyl)-1-[3-(3-hydroxypropyl)phenyl]-6-(4-morpholinylmethyl)-4-oxo-1,4-dihydro-3-quinolinecarboxamide [H.4, W=morpholinylmethyl, Z=3-hydroxypropyl, X=Cl.

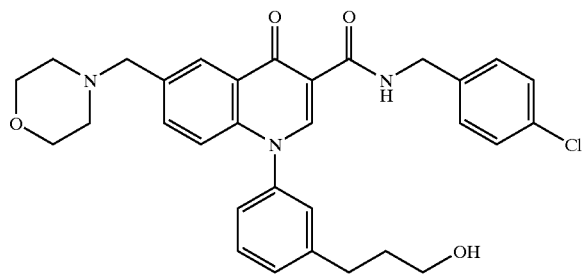

The title compound is prepared according to general preparation H.4 employing N-(4-chlorobenzyl)-1-(3-(3-hydroxy-1-propynyl)phenyl)-6-(4-morpholinylmethyl)-4-oxo-1,4-dihydro-3-quinolinecarboxamide (Example 20, 0.300 g) in a solution of methanol/$CH_2Cl_2$ (4/1, 50 mL) and 10% Pd/C (60 mg). The crude product is purified by column chromatography ($CH_2Cl_2$/methanol, 97.5/2.5, 96/4). The resulting solid is recrystallized from methanol to afford 150 mg (50%) of the title compound as a white solid. Physical characteristics: M.p. 115–118° C.; $^1$H NMR (300 MHz, DMSO-$d_6$) δ 10.36, 8.58, 8.29, 7.68, 7.58, 7.53–7.45, 7.43–7.35, 7.06, 4.58, 4.51, 3.60–3.55, 3.41, 2.74, 2.37, 1.68–1.60; C NMR (75 MHz, CDCl$_3$) δ 176.9, 165.1, 147.5, 145.0, 140.7, 140.0, 137.5, 135.7, 133.7, 130.3, 129.0, 128.7, 127.1, 127.0, 126.8, 124.6, 118.2, 111.9, 67.0, 62.6, 61.7, 53.6, 42.7, 33.9, 31.8; IR (diffuse reflectance) 2947, 2351 (w), 2318 (w), 1964 (w), 1940 (w), 1916 (w), 1657 (s), 1600, 1574, 1544, 1488 (s), 1356, 1323, 1113, 811 cm$^1$. Anal. Calcd for $C_{31}H_{32}ClN_3O_4$: C, 68.18; H, 5.91; N, 7.70; Cl, 6.49. Found: C, 68.43; H, 6.30; N, 7.37; Cl, 6.07.

Testing of Incentive Compounds

The antiviral activity of a compound of the invention can be determined using pharmacological models which are well known to the art, or using Test A described below.

While many of the compounds of the present invention can demonstrate activity against the CMV polymerase, these compounds may be active against the cytomegalovirus by this or other mechanisms of action. Thus, the description below of these compounds' activity against the CMV polymerase is not meant to limit the present invention to a specific mechanism of action.

The HCMV polymerase assay is performed using a scintillation proximity assay (SPA) as described in several references, such as N.D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-cholamidopropyl)-dimethylammonio]-1-propanesulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 pl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25 C or 37 C H$_2$O bath and terminated via the addition of 40 μl/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37 C, then equilibrated to room temperature, and counted on a Packard Topcount. Linear regressions are performed and IC$_{50}$'s are calculated using computer software. A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of representative compounds of formula I in this assay are shown in Table 1 below.

TABLE 1

| | Polymerase IC$_{50}$ (μM) | | |
| Example | HCMV | HSV | VZV |
| --- | --- | --- | --- |
| 1 | 0.81 | 0.55 | 0.4 |
| 2 | 3.0 | nd | nd |
| 3 | 2.1 | nd | nd |
| 4 | 1.1 | nd | nd |
| 5 | 4.0 | nd | nd |
| 6 | 1.1 | nd | nd |
| 7 | 2.0 | nd | nd |
| 8 | 1.47 | nd | nd |
| 9 | 1.32 | nd | nd |
| 10 | 0.89 | nd | nd |
| 11 | 1.18 | nd | nd |
| 12 | 2.2 | nd | nd |
| 13 | 0.73 | 0.54 | 0.24 |
| 14 | 0.82 | 0.7 | 0.43 |
| 15 | 1.7 | nd | nd |
| 16 | 1.9 | nd | nd |
| 17 | 0.74 | 0.44 | 0.31 |
| 18 | 1.21 | nd | nd |
| 19 | 1.05 | nd | nd |
| 20 | 0.57 | 0.59 | 0.29 |
| 21 | 1.13 | nd | ml |
| 22 | 0.93 | nd | nd |
| 23 | 0.76 | nd | nd |
| 24 | 0.68 | nd | nd |
| 25 | 1.08 | 0.98 | 0.48 | nd not determined.

Having described the invention in detail and by reference to the preferred embodiments thereof, it will be apparent that modifications and variations are possible without departing from the scope of the appended claims.

What is claimed is:

1. A compound of formula I,

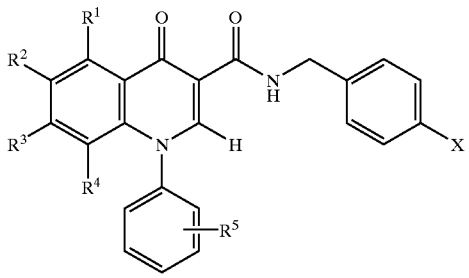

wherein,

X is Cl, F, Br, CN, or $NO_2$;

$R^1$ is H, halo, or $C_{1-4}$alkyl optionally substituted by one to three halo;

$R^2$ is
- (a) H,
- (b) halo,
- (c) aryl,
- (d) het, wherein said het is bound via a carbon atom,
- (e) $C_{1-7}$alkyl which may be partially unsaturated and optionally substituted by one or more substituents of the group $R^{10}$, $NR^7R^8$, halo, $(C=O)R^6$, or $S(O)_mR^6$,
- (f) $NR^7R^8$,
- (g) $OR^{11}$,
- (h) $SR^{11}$,
- (i) $NHSO_2R$
- (j) $S(O)_mR^6$,
- (k) $(C=O)R^6$,
- (l) $(C=O)OR^{11}$,
- (m) CHO,
- (n) cyano, or
- (o) $C_{3-8}$cycloalkyl which may be partially unsaturated and is optionally substituted by one or more substituents selected from halo, oxo, $R^{10}$, $C_{1-7}$alkyl, or $NR^7R^8$;

$R^3$ is
- (a) H,
- (b) halo,
- (c) $OR^{11}$, or
- (d) $C_{1-7}$alkyl which may be partially unsaturated and optionally substituted by one or more substituents of the group $OR^{11}$, $SR^{11}$, $NR^7R^8$, or halo, or $R^2$ together with $R^3$ form a carbocyclic or saturated 5 or 6 membered het which may be optionally substituted by $NR^7R^8$, het attached through a carbon atom, or $C_{1-7}$alkyl which may be optionally substituted by $OR^{12}$;

$R^4$ is
- (a) H,
- (b) halo,
- (c) $OR^{11}$, or
- (d) $C_{1-7}$alkyl which may be partially unsaturated and optionally substituted by one or more substituents of the group $OR^{11}$, $SR^{11}$, $NR^7R^8$, aryl, halo, $C_{3-8}$cycloalkyl optionally substituted by $OR^{12}$, or het attached through a carbon atom, or
- (e) $NR^7R^8$;

$R^5$ is
- (a) H,
- (b) halo,
- (c) $OR^{11}$,
- (d) $O(CH_2CH_2O)_nR^{12}$,
- (e) $C_{3-8}$cycloalkyl which may be partially unsaturated and is optionally substituted by one or more substituents selected from halo, $OR^{12}$, $SR^{12}$, oxo, $C_{1-7}$alkyl or $NR^{12}R^{12}$,
- (f) het,
- (g) aryl,
- (h) $NHSO_2R^6$,
- (i) $S(O)_mR^6$,
- (j) $(C=O)R^6$,
- (k) $(C=O)OR^{11}$,
- (l) nitro,
- (m) cyano,
- (n) $SR^{11}$,
- (o) $NR^7R^8$,
- (p) $C_{1-7}$alkyl which may be partially unsaturated and is optionally substituted by one or more substituents selected from $NR^7R^8$, $R^{10}$, $S(O)_mR^6$, $(P=O)(OR^{12})_2$, $(C=O)R^6$, or halo,
- (q) CHO,
- (r) SCN,
- (s) Any two adjacent $R^5$ substituents taken with the bond connecting them form an aryl, or het, or
- (t) Any two adjacent $R^5$ substituents taken together constitute a $C_{3-6}$alkyl chain which may be optionally substituted by $R^9$, $NR^7R^8$, cyano, $CO_2R^{12}$, $OR^{11}$, $SR^{11}$, or $(=O)$;

$R^6$ is
- (a) $C_{1-7}$alkyl,
- (b) $NR^{11}R^{11}$,
- (c) aryl, or
- (d) het;

$R^7$ and $R^8$ are independently
- (a) H,
- (b) aryl,
- (c) $C_{1-7}$alkyl which may be partially unsaturated and is optionally substituted by one or more substituents selected from $S(O)_mR^6$, $CONR^{12}R^{12}$, $CO_2R^{12}$, $(C=O)R^9$, het, aryl, cyano, or halo,
- (d) $C_{2-7}$alkyl which may be partially unsaturated and is substituted by one or more substituents selected from $NR^{12}R^{12}$, $OR^{11}$, or $SR^{11}$,
- (e) $C_{3-8}$cycloalkyl which may be partially unsaturated and is optionally substituted by one or more substituents selected from halo, $OR^{12}$, $SR^{12}$, oxo, or $NR^{12}R^{12}$,
- (f) $(C=O)R^9$, or
- (g) $R^7$ and $R^8$ together with the nitrogen to which they are attached for a het;

$R^9$ is
- (a) aryl,
- (b) het, wherein said het is bound through a carbon atom,
- (c) $C_{1-7}$alkyl optionally substituted by aryl, het, cyano, $OR^{12}$, $SR^{12}$, $NR^{12}R^{12}$, or halo, or
- (d) $C_{3-8}$cycloalkyl which may be partially unsaturated and is optionally substituted by one or more substituents selected from halo, $OR^{12}$, $SR^{12}$, or $NR^{12}R^{12}$;

R¹⁰ is
- (a) OR¹¹,
- (b) SR¹¹,
- (c) CO$_2$R²,
- (d) het,
- (e) aryl, or
- (f) cyano;

R¹¹ is
- (a) H,
- (b) aryl,
- (c) het, wherein said het is bound through a carbon atom,
- (d) C$_{1-7}$alkyl optionally substituted by aryl, het wherein said het is bound through a carbon atom, C$_{3-8}$ cycloalkyl optionally substituted by OR¹², or halo,
- (e) C$_{2-7}$alkyl substituted by OR¹², SR¹², or NR¹²R¹², or
- (f) C$_{3-8}$cycloalkyl which may be partially unsaturated and is optionally substituted by one or more substituents selected from halo, OR¹², SR¹², or NR¹²R¹², R¹² is H, or C$_{1-7}$alkyl;

each m is independently 1 or 2;

each n is independently 1, 2, or 3;

wherein aryl is a phenyl radical or an ortho-fused bicyclic carbocyclic radical wherein at least one ring is aromatic and is optionally substituted with one or more substituents selected from halo, OH, cyano, CO$_2$R¹², CF$_3$, CF$_{1-6}$alkoxy, or C$_{1-6}$alkyl which may be further substituted by one to three SR¹², NR¹²R¹², OR¹², or CO$_2$R¹² groups;

wherein het is a four-(4), five-(5), six-(6), or seven-(7) membered saturated or unsaturated heterocyclic ring having 1, 2, or 3 heteroatoms selected from oxygen, sulfur, or nitrogen, which is optionally fused to a benzene ring, or any bicyclic heterocyclic group and wherein any het is optionally substituted with one or more substituents selected from halo, OH, cyano, phenyl, CO$_2$R¹², CF$_3$, C$_{1-6}$alkoxy, oxo, oxime, or C$_{1-6}$ alkyl which may be further substituted by one to three SR¹², NR¹²R¹², OR¹², or CO$_2$R¹² groups; and wherein halo is F, Cl, Br, I;

and pharmaceutically acceptable salts thereof.

2. The compound according to claim 1, wherein:
X is Cl;
R¹ is H;
R² is C$_{1-7}$alkyl which may be partially unsaturated and is substituted by one or more substituents of the group OH, NR⁷R⁸, or het bound through a carbon atom; and
R³ is H.

3. The compound according to claim 1, wherein R² is C$_{1-7}$alkyl which may be partially unsaturated and is substituted by one or more substituents of the group OH, NR⁷R⁸, or het bound through a carbon atom.

4. The compound according to claim 3 wherein R² is C$_{1-7}$alkyl which is fully saturated and is substituted by one or more substituents of the group OH or NR⁷R⁸.

5. The compound according to claim 1 wherein R² is 3-hydroxypropyl.

6. The compound according to claim 1 wherein R² is 3-hydroxy-1-propynyl.

7. The compound according to claim 1 wherein R² is tetrahydro-2H-pyran-4-ylmethyl.

8. The compound according to claim 1 wherein R² is 4-morpholinylmethyl.

9. The compound according to claim 1 which is selected from the group consisting of (1) N-(4-chlorobenzyl)-6-(4-morpholinylmethyl)-4-oxo-1-phenyl-1,4-dihydro-3-quinolinecarboxamide;

(2) N-(4-chlorobenzyl)-6-(3-hydroxypropyl)-4-oxo-1-phenyl-1,4-dihydro-3-quinoline-carboxamide;

(3) N-(4-chlorobenzyl)-6-(3-hydroxy-1-propynyl)-4-oxo-1-phenyl-1,4-dihydro-3-quinolinecarboxamide;

(4) N-(4-chlorobenzyl)-4-oxo-1-phenyl-6-(tetrahydro-2H-pyran-4-ylmethyl)-1,4-dihydro-3-quinolinecarboxamide;

(5) N-(4-chlorobenzyl)-1-(2-methylphenyl)-6-(4-morpholinylmethyl)-4-oxo-1,4-dihydro-3-quinolinecarboxamide (6) N-(4-chlorobenzyl)-1-(3-iodophenyl)-6-(4-morpholinylmethyl)-4-oxo-1,4-dihydro-3-quinolinecarboxamideN-(4-chlorobenzyl)-1-(4-chlorophenyl)-6-(4-morpholinylmethyl)-4-oxo-1,4-dihydro-3-quinolinecarboxamide;

(7) N-(4-chlorobenzyl)-1-(4-isopropylphenyl)-6-(4-morpholinylmethyl)-4-oxo-1,4-dihydro-3-quinolinecarboxamide (8) N-(4-chlorobenzyl)-1-(4-methoxyphenyl)-6-(4-morpholinylmethyl)-4-oxo-1,4-dihydro-3-quinolinecarboxamide;

(9) N-(4-fluorobenzyl)-1-(4-chlorophenyl)-6-(4-morpholinylmethyl)-4-oxo-1,4-dihydro-3-quinolinecarboxamide

(10) N-(4-chlorobenzyl)-6-(4-morpholinylmethyl)-4-oxo-1-(2,4-difluorophenyl)-1,4-dihydro-3-quinolinecarboxamide;

(11) N-(4-chlorobenzyl)-6-(3-hydroxypropyl)-4-oxo-1-(2,4-difluorophenyl)-1,4-dihydro-3-quinolinecarboxamide;

(12) N-(4-chlorobenzyl)-6-(3-hydroxy-1-propynyl)-4-oxo-1-(2,4-difluorophenyl)-1,4-dihydro-3-quinolinecarboxamide;

(13) N-(4-chlorobenzyl)-4-oxo-1-(2,4-difluorophenyl)-6-(tetrahydro-2H-pyran-4-yl-methyl)-1,4-dihydro-3-quinolinecarboxamide;

(14) N-(4-Chlorobenzyl)-1-(2-(hydroxymethyl)phenyl)-6-(4-morpholinylmethyl)-4-oxo-1,4-dihydro-3-quinolinecarboxamide

(15) N-(4-Chlorobenzyl)-1-(2,3-dihydro-1H-inden-5-yl)-6-(4-morpholinylmethyl)-4-oxo-1,4-dihydro-3-quinolinecarboxamide;

(16) 1-(1,3-Benzodioxol-5-yl)-N-(4-chlorobenzyl)-6-(4-morpholinylmethyl)-4-oxo-1,4-dihydro-3-quinolinecarboxamide;

(17) N-(4-Chlorobenzyl)-1-(1H-indol-5-yl)-6-(4-morpholinylmethyl)-4-oxo-1,4-dihydro-3-quinolinecarboxamide

(18) N-(4-Fluorobenzyl)-1-(1H-indol-5-yl)-6-(4-morpholinylmethyl)-4-oxo-1,4-dihydro-3-quinolinecarboxamide

(19) N-(4-Chlorobenzyl)-1-(3-hydroxyphenyl)-6-(4-morpholinylmethyl)4-oxo-1,4-dihydro-3-quinolinecarboxamide

(20) N-(4-Chlorobenzyl)-1-(3-(2-hydroxyethyl)phenyl)-6-(4-morpholinylmethyl)-4-oxo-1,4-dihydro-3-quinolinecarboxamide

(21) N-(4-Fluorobenzyl)-1-(3-(2-hydroxyethyl)phenyl)-6-(4-morpholinylmethyl)-4-oxo-1,4-dihydro-3-quinolinecarboxamide

(22) N-(4-chlorobenzyl)-1-(3-methoxyphenyl)-6-(4-morpholinylmethyl)-4-oxo-1,4-dihydro-3-quinolinecarboxamide

(23) N-(4-chlorobenzyl)-1-(3-(hydroxymethyl)phenyl)-6-(4-morpholinylmethyl)-4-oxo-1,4-dihydro-3-quinolinecarboxamide

(24) N-(4-chlorobenzyl)-6-(4-morpholinylmethyl)-1-(4-(4-morpholinyl)phenyl)-4-oxo-1,4-dihydro-3-quinolinecarboxamide

(25) N-(4-chlorobenzyl)-1-(3,4-difluorophenyl)-6-(4-morpholinylmethyl)-4-oxo-1,4-dihydro-3-quinolinecarboxamide

(26) N-(4-chlorobenzyl)-1-(3-(3-hydroxy-1-propynyl)phenyl)-6-(4-morpholinylmethyl)-4-oxo-1,4-dihydro-3-quinolinecarboxamide

(27) N-(4-chlorobenzyl)-1-(3-(4-hydroxy-1-butynyl)phenyl)-6-(4-morpholinylmethyl)-4-oxo-1,4-dihydro-3-quinolinecarboxamide

(28) N-(4-chlorobenzyl)-1-(3-(4-hydroxy-1-butynyl)phenyl)-6-(4-morpholinylmethyl)-4-oxo-1,4-dihydro-3-quinolinecarboxamide;

(29) N-(4-chlorobenzyl)-1-(3-(5-hydroxypentyl)phenyl)-6-(4-morpholinylmethyl)-4-oxo-1,4-dihydro-3-quinolinecarboxamide;

(30) N-(4-chlorobenzyl)-1-(3-(4-hydroxybutyl)phenyl)-6-(4-morpholinylmethyl)-4-oxo-1,4-dihydro-3-quinolinecarboxarnide;

(31) N-(4-chlorobenzyl)-1-[3-(3-hydroxypropyl)phenyl]-6-(4-morpholinylmethyl)-4-oxo-1,4-dihydro-3-quinolinecarboxamide;

and pharmaceutically acceptable salts thereof.

10. The compound according to claim 9 which is N-(4-chlorobenzyl)-6-(4-morpholinylmethyl)-4-oxo-1-phenyl-1,4-dihydro-3-quinolinecarboxamide or a pharmaceutically acceptable salt thereof.

11. The compound according to claim 1 wherein X is Cl.

12. The compound according to claim 1 wherein either $R^2$ or $R^4$ or both $R^2$ and $R^4$ do not represent H.

13. A pharmaceutical composition comprising a compound of claim 1 and a pharmaceutically acceptable carrier.

14. The composition according to claim 13, wherein:

X is Cl;

$R^1$ is H;

$R^2$ is $C_{1-7}$alkyl which may be partially unsaturated and is substituted by one or more substituents of the group OH or $NR^7R^8$, or het bound through a carbon atom, and $R^3$ is H.

15. The composition according to claim 13, wherein $R^2$ is $C_{1-7}$alkyl which may be partially unsaturated and is substituted by one or more substituents of the group OH or $NR^7R^8$, or het bound through a carbon atom.

16. The composition according to claim 15 wherein $R^2$ is $C_{1-7}$alkyl which is fully saturated and is substituted by one or more substituents of the group OH or $NR^7R^8$.

17. The composition according to claim 13 wherein $R^2$ is 3-hydroxypropyl.

18. The composition according to claim 13 wherein $R^2$ is 3-hydroxy-1-propynyl.

19. The composition according to claim 13 wherein $R^2$ is tetrahydro-2H-pyran-4-ylmethyl.

20. The composition according to claim 13 wherein $R^2$ is 4-morpholinylmethyl.

21. The composition according to claim 13 wherein said compound is selected from the group consisting of (1) N-(4-chlorobenzyl)-6-(4-morpholinylmethyl)-4-oxo-1-phenyl-1,4-dihydro-3-quinolinecarboxamide;

(2) N-(4-chlorobenzyl)-6-(3-hydroxypropyl)-4-oxo-1-phenyl-1,4-dihydro-3-quinoline-carboxamide;

(3) N-(4-chlorobenzyl)-6-(3-hydroxy-1-propynyl)-4-oxo-1-phenyl-1,4-dihydro-3-quinolinecarboxamide;

(4) N-(4-chlorobenzyl)-4-oxo-1-phenyl-6-(tetrahydro-2H-pyran-4-ylmethyl)-1,4-dihydro-3-quinolinecarboxamide;

(5) N-(4-chlorobenzyl)-1-(2-methylphenyl)-6-(4-morpholinylmethyl)-4-oxo-1,4-dihydro-3-quinolinecarboxamide;

(6) N-(4-chlorobenzyl)-1-(3-iodophenyl)-6-(4-morpholinylmethyl)-4-oxo-1,4-dihydro-3-quinolinecarboxamide;

(7) N-(4-chlorobenzyl)-1-(4-chlorophenyl)-6-(4-morpholinylmethyl)-4-oxo-1,4-dihydro-3-quinolinecarboxamide;

(8) N-(4-chlorobenzyl)-1-(4-isopropylphenyl)-6-(4-morpholinylmethyl)-4-oxo-1,4-dihydro-3-quinolinecarboxamide;

(9) N-(4-chlorobenzyl)-1-(4-methoxyphenyl)-6-(4-morpholinylmethyl)-4-oxo-1,4-dihydro-3-quinolinecarboxamide;

(10) N-(4-fluorobenzyl)-1-(4-chlorophenyl)-6-(4-morpholinylmethyl)-4-oxo-1,4-dihydro-3-quinolinecarboxamide;

(11) N-(4-chlorobenzyl)-6-(4-morpholinylmethyl)-4-oxo-1-(2,4-difluorophenyl)-1,4-dihydro-3-quinolinecarboxamide;

(12) N-(4-chlorobenzyl)-6-(3-hydroxypropyl)-4-oxo-1-(2,4-difluorophenyl)-1,4-dihydro-3-quinolinecarboxamide;

(13) N-(4-chlorobenzyl)-6-(3-hydroxy-1-propynyl)-4-oxo-1-(2,4-difluorophenyl)-1,4-dihydro-3-quinolinecarboxamide;

(14) N-(4-chlorobenzyl)-4-oxo-1-(2,4-difluorophenyl)-6-(tetrahydro-2H-pyran-4-yl-methyl)-1,4-dihydro-3-quinolinecarboxamide;

(15) N-(4-Chlorobenzyl)-1-(2-(hydroxymethyl)phenyl)-6-(4-morpholinylmethyl)-4-oxo-1,4-dihydro-3-quinolinecarboxamide;

(16) N-(4-Chlorobenzyl)-1-(2,3-dihydro-1H-inden-5-yl)-6-(4-morpholinylmethyl)-4-oxo-1,4-dihydro-3-quinolinecarboxamide;

(17) 1-(1,3-Benzodioxol-5-yl)-N-(4-chlorobenzyl)-6-(4-morpholinylmethyl)-4-oxo-1,4-dihydro-3-quinolinecarboxamide;

(18) N-(4-Chlorobenzyl)-1-(1H-indol-5-yl)-6-(4-morpholinylmethyl)-4-oxo-1,4-dihydro-3-quinolinecarboxamide;

(19) N-(4-Fluorobenzyl)-1-(1H-indol-5-yl)-6-(4-morpholinylmethyl)-4-oxo-1,4-dihydro-3-quinolinecarboxamnide;

(20) N-(4-Chlorobenzyl)-1-(3-hydroxyphenyl)-6-(4-morpholinylmethyl)-4-oxo-1,4-dihydro-3-quinolinecarboxamide;

(21) N-(4-Chlorobenzyl)-1-(3-(2-hydroxyethyl)phenyl)-6-(4-morpholinylmethyl)-4-oxo-1,4-dihydro-3-quinolinecarboxamide;

(22) N-(4-Fluorobenzyl)-1-(3-(2-hydroxyethyl)phenyl)-6-(4-morpholinylmethyl)-4-oxo-1,4-dihydro-3-quinolinecarboxamide;

(23) N-(4-chlorobenzyl)-1-(3-methoxyphenyl)-6-(4-morpholinylmethyl)-4-oxo-1,4-dihydro-3-quinolinecarboxamide;

(24) N-(4-chlorobenzyl)-1-(3-(hydroxymethyl)phenyl)-6-(4-morpholinylmethyl)-4-oxo-1,4-dihydro-3-quinolinecarboxamide;

(25) N-(4-chlorobenzyl)-6-(4-morpholinylmethyl)-1-(4-(4-morpholinyl)phenyl)-4-oxo-1,4-dihydro-3-quinolinecarboxamide;

(26) N-(4-chlorobenzyl)-1-(3,4-difluorophenyl)-6-(4-morpholinylmethyl)-4-oxo-1,4-dihydro-3-quinolinecarboxamide;

(27) N-(4-chlorobenzyl)-1-(3-(3-hydroxy-1-propynyl)phenyl)-6-(4-morpholinylmethyl)-4-oxo-1,4-dihydro-3-quinolinecarboxamide;

(28) N-(4-chlorobenzyl)-1-(3-(4-hydroxy-1-butynyl)phenyl)-6-(4-morpholinylmethyl)-4-oxo-1,4-dihydro-3-quinolinecarboxamide;

(29) N-(4-chlorobenzyl)-1-(3-(4-hydroxy-1-butynyl)phenyl)-6-(4-morpholinylmethyl)-4-oxo-1,4-dihydro-3-quinolinecarboxamide;

(30) N-(4-chlorobenzyl)-1-(3-(5-hydroxypentyl)phenyl)-6-(4-morpholinylmethyl)-4-oxo-1,4-dihydro-3-quinolinecarboxamide;

(31) N-(4-chlorobenzyl)-1-(3-(4-hydroxybutyl)phenyl)-6-(4-morpholinylmethyl)-4-oxo-1,4-dihydro-3-quinolinecarboxamide;

(32) N-(4-chlorobenzyl)-1-[3-(3-hydroxypropyl)phenyl]-6-(4-morpholinylmethyl)-4-oxo-1,4-dihydro-3-quinolinecarboxamide;

and pharmaceutically acceptable salts thereof.

22. The composition according to claim 21 wherein said compound is N-(4-chlorobenzyl)-6-(4-morpholinylmethyl)-4-oxo-1-phenyl-1,4-dihydro-3-quinolinecarboxamide or a pharmaceutically acceptable salt thereof.

23. The composition according to claim 13 wherein X is Cl.

24. The composition according to claim 13 wherein either $R^2$ or $R^4$ or both $R^2$ and $R^4$ do not represent H.

25. A method for treating a herpes viral infection in the mammal comprising administering a therapeutically effective amount of a compound or composition of any one of claims 1 to 24 to said mammal.

26. The method of claim 25 wherein said mammal is a human.

27. The method of claim 25 wherein said mammal is a livestock or companion animal.

28. The method of claim 25 wherein the infection is herpes simplex virus type 1 or 2, herpes human virus type, 6, 7, or 8, varicella zoster virus, human cytomegalovirus, or Epstein-Barr virus.

29. The method of claim 25 wherein the infection is herpes simplex virus type 1 or 2, herpes human virus type 8, varicella zoster virus, human cytomegalovirus, or Epstein-Barr virus.

30. The method of claim 25 wherein said compound is administered in an amount from about 0.1 to about 300 mg/kg of body weight.

31. The method of claim 30 wherein the amount administered is from about 1 to about 30 mg/kg of body weight.

32. The method of claim 25 wherein said compound is administered parenterally, topically, intravaginally, orally, or rectally.

* * * * *